(12) United States Patent
Murphy-Ullrich et al.

(10) Patent No.: US 6,458,767 B1
(45) Date of Patent: Oct. 1, 2002

(54) USE OF PEPTIDES INHIBITORY FOR THROMBOSPONDIN DEPENDENT TGF-β ACTIVATION IN THE TREATMENT OF KIDNEY DISEASE

(75) Inventors: Joanne E. Murphy-Ullrich; Solange M. F. Ribeiro, both of Birmingham, AL (US); Christian Hugo, Weideu/Opt (DE); David D. Roberts; Henry C. Krutzsch, both of Bethesda, MD (US)

(73) Assignee: The UAB Research Foundation, Birmingham, AL (US)

( * ) Notice: Subject to any disclaimer, the term of this patent is extended or adjusted under 35 U.S.C. 154(b) by 0 days.

(21) Appl. No.: 09/321,932

(22) Filed: May 28, 1999

Related U.S. Application Data

(63) Continuation-in-part of application No. 08/871,561, filed on Jun. 10, 1997, now Pat. No. 6,384,189, which is a continuation of application No. 08/238,169, filed on May 4, 1994, now abandoned.

(51) Int. Cl.$^7$ .............................................. A61K 38/07
(52) U.S. Cl. ...................................................... 514/18
(58) Field of Search ........................................... 514/18

(56) References Cited

U.S. PATENT DOCUMENTS

| | | | |
|---|---|---|---|
| 4,439,196 A | 3/1984 | Higuchi | 604/890 |
| 4,447,224 A | 5/1984 | DeCant, Jr. et al. | 604/67 |
| 4,447,233 A | 5/1984 | Mayfield | 604/152 |
| 4,475,196 A | 10/1984 | La Zor | 371/29 |
| 4,486,194 A | 12/1984 | Ferrara | 604/897 |
| 4,487,603 A | 12/1984 | Harris | 604/152 |

OTHER PUBLICATIONS

Akagi et al. (1996) Inhibition of TGF-β1 expression by antisense oligonucleotides suppressed extracellular matrix accumulation in experimental glomerulonephritis. Kidney Int., 50:148–155.
Barcellos–Hoff (1996) Latency and aCtivation in the Control of TGF-β J. Mam. Gland. Biol. Neoplasia, 1:351–361.
Bornstein (1995) Diversity of function is inherent in matricellular proteins: an appraisal of Thrombospondin 1. J. Cell Biol., 130:503–506.
Bornstein (1992) Thrombospondins: structure and regulation of expression FASEB, vol. 6, pp. 3290–3299.
Border et al. (1994) Transforming growth factorβ in tissue fibrosis. N. Engl. J. Med., 331:1286–1292.
Border et al. (1992) Natural inhibitor of transforming growth factor–β protects against scarring in experimental kidney disease. Nature, 360:361–364.
Border et al. (1990) Suppression of experimental glomerulonephritis by antiserum against transforming growth factor β 1 Nature , 346:371–374.
Crawford et al. (1998) Thrombospondin–1 is a major activator of TGF–β 1 in vivo. Cell, 93:1159–1170.

D'Amico (1987) The commonest glomerulonephritis in the world: IgA nephropathy. QJM, 245:709–727.
Duijvestijn et al. (1992) Antibodies defining rat endothelial cells: RECA–1, a pan–endothelial cell–specific monoclonal antibody. Lab. Invest., 66(4):459–466.
Galla (1995) IgA nephropathy. Kidney Int., 47:377–387.
Guo et al. (1997) Antiproliferative and antitumor activities of D–reverse peptides derived from the second type–1 repeat of thrombospondin–1. J. Peptide Res., 50:210–221.
Harpel et al. (1992) Control of transforming growth factor–β activity: latency vs. activation. Prog. Growth Factor Res., 4:321–335.
Hugo et al. (1999) Thrombospondin peptides are potent inhibitors of mesangial and glomerular endothelial cell proliferation in vitro and in vivo. Kidney Int., vol. 55, pp. 2236–2249.
Hugo et al. (1998) Thrombospondin 1 precedes and predicts the development of tubulointerstitial fibrosis in glomerular disease in the rat. Kidney Int., 53:302–311.
Hugo et al. (1997) Extraglomerular origin of the mesangial cell after injury. J. Clin. Invest. , 100:786–794.
Hugo et al. (1996) The cytoskeletal linking proteins, moesin and radixin, are upregulated by platelet–derived growth factor, but not basic fibroblast growth factor in experimental mesangial proliferative glomerulonephritis. J. Clin. Invest., 97(11): 2499–2508.
Hugo et al. (1995) Thrombospondin 1 is expressed by proliferating mesangial cells and is up–regulated by PDGF and bFGF in vivo. Kidney Int., 48:1846–1856.
Iruela–Arispe et al. (1995) Participation of glomerular endothelial cells in the capillary repair of glomerulonephritis. Am. J. Physiol., 147:1715–1727.
Isaka et al. (1996) Gene therapy by skeletal muscle expression of decorin prevents fibrotic disease in rat kidney. Nat. Med., 2:418–423.
Isaka et al. (1993) Glomerulosclerosis induced by in vivo transfection of transforming growth factor–β or platelet–derived growth factor gene into the rat kidney. J. Clin. Invest., 92:2597–2601.

(List continued on next page.)

Primary Examiner—David Saunders
Assistant Examiner—Amy DeCloux
(74) Attorney, Agent, or Firm—Gifford, Krass, Groh, Sprinkle, Anderson & Citkowski, P.C.

(57) ABSTRACT

The present invention provides a method of treating kidney or renal diseases/conditions in a subject by administering to the subject a pharmaceutically effective amount of a purified LAP peptide, a TSP-1 type 1 repeat peptide, or a fragment thereof to interfere with the activation process of TGF-β by thrombospondin-1 to reduce and/or prevent renal damage. The present invention further provides a method of improving renal function in a subject having impaired renal function by administering to the subject a pharmaceutically effective amount of a purified LAP peptide, a TSP-1 type 1 repeat peptide, or a fragment thereof.

13 Claims, 9 Drawing Sheets

OTHER PUBLICATIONS

Johnson (1994) The glomerular response to injury: progression or resolution? Kidney Int., 45(6):1769–82.

Johnson (1991a) Platelet–complement interactions in mesangial proliferative nephritis in the rat. Am. J. Pathol., 138(2):313–21.

Johnson (1991b) Expression of smooth muscle cell phenotype by rat mesangial cells in immune complex nephritis. J. Clin. Invest. 87(3):847–58.

Kaartinen et al. (1995) Abnormal lung development and cleft palate in mice lacking TGF–β 3 indicates defects of epithelial–mesenchymal interaction. Nature Genet., 11:415–421.

Kitamura et al. (1995) Transfer of a mutated gene encoding active transforming growth factor–β 1 suppresses mitogenesis and IL–1 response in the glomerulus. Kidney Int., 48:1747–1757.

Kliem et al. (1996) Mechanisms involved in the pathogenesis of tubulointerstitial fibrosis in 5/6–nephrectomized rats. Kidney Int., 49:666–678.

Kopp et al. (1996) Transgenic mice with increased plasma levels of TGF–β1 develop progressive renal disease. Lab. Invest., 74:991–1003.

Lawler et al. (1998) Thrombospondin–1 is required for normal murine pulmonary homeostasis and its absence causes pneumonia. J. Clin. Invest., 101:982–992.

McGregor et al. (1994) Thrombospondin in human glomerulopathies: a marker of inflammation and early fibrosis. Am. J. Pathol., 144:1281–1287.

Massague et al. (1992) Transforming growth factor–β . Cancer Surveys, vol. 12, pp. 81–103.

Murphy–Ullrich et al. (1992) Transforming growth factor–β complexes with thrombospondin. Molecular Biology of the Cell., vol. 3, pp. 181–188.

Okuda et al. (1990) Elevated expression of transforming growth factor–β and proteoglycan production in experimental glomerulonephritis. J. Clin. Invest., 86:453–462.

Pfeffer et al. (1971) Validity of an indirect tail–cuff method for determining systolic arterial pressure in unanesthetized normotensive and spontaneously hypertensive rats. J. Lab. Clin. Med., 78:957–962.

Ribeiro et al. (1999) The activation sequence of thrombospondin–1 interacts with the latency–associated peptide to regulate activation of latent transforming growth factor–β . J. Biol. Chem., 274–13586–13593.

Sanford et al. (1997) TGFβ 2 knockout mcie have multiple developmental defects that are non–overlapping with other TGF knockout phenotypes. Development, 124:2659–2670.

Schoecklmann et al. (1997) TGF–β 1–induced cell cycle arrest in renal mesangial cells involves inhibition of cyclin E–cdk 2 activation and retinoblastoma protein phosphorylation. Kidney Int., 51:1228–1236.

Schultz–Cherry et al. (1995) Regulation of transforming growth factor–β activation by discrete sequences of thrombospondin 1. J. Biol. Chem., 270:7304–7310.

Schultz–Cherry et al. (1994) Thrombospondin binds and activates the small and large forms of latent transforming growth factor–β in a chemically defined system. J. Biol. Chem., 269:26775–82.

Schultz–Cherry et al. (1993) Thrombospondin causes activation of latent transforming growth factor–secreted by endothelial cells by a novel mechanism. J. Cell Biol., 122:923–932.

Sharma et al. (1994) The emerging role of transforming growth factor–β in kidney diseases. Am. J. Physiol., 266:F829–F842.

Shull et al. (1992) Targeted disruption of the mouse transforming growth factor–β 1 gene results in multifocal inflammatory disease. Nature, 359:693–699.

Sime et al. (1997) Adenovector–mediated gene transfer of active transforming growth factor–β 1 induces prolonged severe fibrosis in rat lung. J. Clin. Invest. 100:768–776.

Skalli et al. (1986) A monoclonal antibody against α–smooth muscle actin: a new probe for smooth muscle diferentiation. J. Cell Biol., 103(6):2787–2796.

Suto et al. (1996) Mesangial cell–dervied transforming growth factor–β 1 reduces macrophage adhesiveness with consequent deactivation. Kidney Int., 50:445–452.

Tada et al. (1998) The fibronectin production is increased by thrombospondin via activation of TGF–β in cultured human mesangial cells. Nephron. 79:38–43.

Wahl (1992) Transforming growth factor beta (TGF–β) in inflammation: a cause and a cure. J. Clin. Immunol., 12:61–74.

USE OF PEPTIDES INHIBITORY FOR THROMBOSPONDIN DEPENDENT TGF-β ACTIVATION IN THE TREATMENT OF KIDNEY DISEASE

RELATED APPLICATIONS

This application is a continuation-in-part of U.S. Ser. No. 08/871,561 filed Jun. 10, 1997, now U.S. Pat. No. 6,384,189 which is a continuation of U.S. Ser. No. 08/238,169, filed May 4, 1994 now abandoned.

FIELD OF THE INVENTION

The present invention generally relates to a method of regulating transforming growth factor TGF-β (TGF-β) activity. More particularly, the present invention relates to a method of interfering with the activation of TGF-β by thrombospondin through the administration of peptides in order to treat kidney diseases and/or conditions.

BACKGROUND OF THE INVENTION

Extracellular matrix accumulation is one of the hallmarks of inflammatory glomerular disease as a major cause of end-stage renal disease in man. Mesangial proliferative glomerulonephritis, the most common type of glomerulonephritis in the Western World (D'Amico (1987) *QJM* 245, 709–727), is characterized by mesangial cell (MC) proliferation, activation, and extracellular matrix expansion (Johnson (1994) *Kidney Int.* 45 (6), 1769–82). In up to 50% of the patients with mesangial proliferative glomerulonephritis, the disease process eventually progresses to end-stage renal disease, since specific treatment is still lacking (Galla (1995) *Kidney Int.* 47, 377–387). Typical features of human mesangial proliferative glomerulonephritis are mimicked by an experimental model in the rat, induced by an antibody against the Thy1-antigen on MC ((Johnson (1994) *Kidney Int.* 45 (6), 1769–82). In this model, a single injection of anti-thymocyte antibody results in an acute, complement-dependent MC injury (days zero to two) with proteinuria, followed by a FGF-2- and PDGF-dependent MC proliferative response that is accompanied by a TGF-β-dependent overproduction of extracellular matrix proteins (days three to ten) (Johnson (1994) *Kidney Int.* 45 (6), 1769–82).

The role of TGF-β as a major profibrotic cytokine in the anti-Thy1 model has been well established (Border et al. (1994) *N. Engl. J. Med.* 331, 1286–1292). It has been demonstrated that TGF-β1 mRNA and protein are increased in the anti-Thy1 model (Okuda et al. (1990) *J. Clin. Invest.* 86, 453–462) and that blocking TGF-β1 by injections with a polyclonal anti-TGF-β1 antibody markedly reduced extracellular matrix accumulation (Border et al. (1990) *Nature* 346, 371–374). Injections with the proteoglycan decorin, a TGF-β1, -2, and -3 binding protein, also suppressed TGF-β-dependent alterations such as extracellular matrix accumulation in the anti-Thy1 model (Border et al. (1992) *Nature* 360, 361–364). The results of these studies by Border and colleagues were confirmed by studies using gene transfer techniques in the anti-Thy1 model. Transfer of antisense oligonucleotides against the TGF-β1 mRNA into the rat kidney suppressed upregulation of glomerular TGF-β1 mRNA and protein as well as extracellular matrix accumulation (Akaki et al. (1996) *Kidney Int.* 50, 148–155). Transfer of decorin cDNA into rat skeletal muscle increased the amount of decorin in skeletal muscle and in the kidney, and again ameliorated glomerular disease by decreasing matrix formation (Isaka et al. (1996) *Nat. Med.* 2, 418–423). In contrast, mice transgenic for an active form of TGF-β1 exhibit elevated plasma levels of TGF-β1 and develop progressive renal disease characterized by MC matrix accumulation, interstitial fibrosis, and proteinuria (Kopp et al. (1996) *Lab. Invest.* 74, 991–1003). Transfer of the TGF-β1 gene into glomeruli of normal rats caused an increase in glomerular TGF-β1 protein that was linked to extracellular matrix formation (Isaka et al (1993) *J. Clin. Invest.* 92, 2597–2601). The potential importance of TGF-β in mediating fibrosis also in human kidney disease has been supported by the widespread link of TGF-β upregulation and extracellular matrix excess in many different types of human kidney disease (Border et al. (1994) *N. Engl. J. Med.* 331, 1286–1292).

While these studies suggest great benefit from suppression of TGF-β function in fibrotic kidney disease, it has to be considered that TGF-β is a multifunctional cytokine that exhibits other essential functions in mammals. Mice lacking either the TGF-β1, or -2, or -3 gene do not survive beyond a few weeks after birth (Shull et al. (1992) *Nature* 359, 693–699; Sanford et al. (1997) *Development* 124, 2659–2670; Kaartinen et al. (1995) *Nature Genet.* 11, 415–421). TGF-β1 null mice die a few weeks after birth from a severe generalized inflammatory response demonstrating that complete suppression of TGF-β function must not be a therapeutic goal in treating inflammatory kidney disease (Shull et al. (1992) *Nature* 359, 693–699). Therefore, accurate regulation of TGF-β function seems to be critical for the health of mammals and any anti-TGF-β therapeutic approach should try to target the local overproduction (-function) of TGF-β as specifically as possible.

One possibility to approach this goal could be by controlling (interfering with) the activation process of locally produced TGF-β. TGF-β is secreted by most cell types as a latent, inactive procytokine-complex that consists of the mature, active TGF-β protein, which is noncovalently bound to a dimer of its N-terminal propeptide, the so-called latency-associated protein (LAP), and variably to a latent TGF-β binding protein (LTBP) (Harpel et al. (1992) *Prog. Growth Factor Res.* 4, 321–335). The mature TGF-β protein has to be extracellularly released or unmasked from this procytokine-complex to be able to interact with its receptors. While various players/mechanisms such as pH changes, gamma irradiation, reactive oxygen species, plasmin, calpain, cathepsin, or thrombospondin 1 (TSP1) have been identified to activate TGF-β under in vitro conditions, it is still unknown how TGF-β is activated in an inflammatory process in vivo (Harpel et al. (1992) *Prog. Growth Factor Res.* 4, 321–335).

Recent data have suggested the homotrimeric extracellular matrix protein TSP1 as an activator of TGF-β1 in vitro in different cell systems including MC (Schultz-Cherry et al. (1993) *J. Cell Biol.* 122, 923–932; Tada et al. (1998) *Nephron* 79, 38–43; Schultz-Cherry et al. (1994) *J. Biol. Chem.* 269, 26775–82) as well as in cell free systems. It has been demonstrated that TSP1 forms a trimolecular complex with the TGF-β procytokine-complex by interacting with the mature TGF-β protein as well as the LAP (Ribeiro et al. (1999) *J. Biol. Chem.* 274, 13586–13593). Hereby, the hexapeptide (AA or GG) WSHW (SEQ ID NO:22 or SEQ ID NO:3, respectively) from the type I repeats of the TSP1 molecule is required for TSP1-binding to the mature TGF-β protein facilitating interaction of the KRFK-amino acid sequence (SEQ. ID NO:5) of the TSP1 molecule with the N-terminal LSKL-sequence (SEQ ID NO:21) of the LAP (Schultz-Cherry et al. (1995) *J. Biol. Chem.* 270, 7304–7310; Ribeiro et al. (1999) *J. Biol. Chem.* 274, 13586–13593). This complex interaction is thought to induce a conformational change probably within the LAP that allows the mature TGF-β protein to bind to its receptors. It has been shown that both the hexapeptide AAWSHW (SEQ. ID NO:22) and the LSKL (SEQ. ID NO:21) peptides are able to block activation of TGF-β by TSP1. In addition, comparing TSP1 null mice with TGF-β1 null mice, Crawford et al. identified TSP1 as a major activator of TGF-β1 in vivo during mouse post-natal development (Crawford et al. (1998) Cell 93, 1159–1170). Organ pathology of TGF-β1 null pups and TSP1 null pups were strikingly similar and could be induced in wild type pups by intraperitoneal (i.p.) treatment with the LSKL-peptide that specifically blocks activation of TGF-β1 by TSP1. Loss of TSP1 expression in TSP1 null mice spontaneously produced inflammatory lung disease (Lawler et al. (1998) J. Clin. Invest. 101, 982–992) and histological changes in TSP1 null mice reverted toward wild type by treatment with the TGF-β activating peptide KRFK (SEQ ID NO:5).

Interestingly, TSP1 expression in vitro is regulated by various cytokines such as PDGF, FGF-2, or TGFβ, and is frequently expressed de novo at sites of inflammation and wound heating (Bornstein (1995) J. Cell Biol. 130, 503–506). The involvement of TSP1 in the anti-Thy1 model has been demonstrated (Hugo et al. (1995) Kidney Int. 48, 1846–1856). In the anti-Thy1 model of mesangial proliferative glomerulonephritis, a marked transient de novo expression of TSP1 by MC (peak on day five) was regulated by FGF-2 and PDGF (Hugo et al. (1995) Kidney Int. 48, 1846–1856) and coincided with the upregulation of TGF-β1 (Okuda et al. (1990) J. Clin. Invest. 86, 453–462).

Therefore, it is hypothesized that TSP1 is a major endogenous activator of TGF-β in inflammatory kidney disease and it was investigated whether systemic treatment with either one of two different peptides that block activation of TGF-β1 by TSP1 is able to suppress activation and function of TGF-β in experimental mesangial proliferative nephritis in the rat.

Accordingly, it would be advantageous and desirable to have a method for treating inflammatory kidney diseases, including mesangial proliferative glomerulonephritis, by treating a subject in need of such treatment with a peptide capable of blocking the activation of TGF-β1.

SUMMARY OF THE INVENTION

The present invention provides a method of treating kidney or renal diseases/conditions in a subject by administering to the subject a pharmaceutically effective amount of a purified peptide including the LAP domain peptide, the TSP-1 type 1 domain peptide, or fragments thereof to interfere with the activation process of TGF-β to reduce and/or prevent renal damage.

The present invention further provides a method of improving renal function in a subject having impaired renal function by administering to the subject a pharmaceutically effective amount of a purified peptide including the LAP domain peptide, the TSP-1 type 1 domain peptide, or fragments thereof

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended Figures. These Figures form a part of the specification. It is to be noted, however, that the appended Figures illustrate preferred embodiments of the invention and therefore are not to be considered limiting in their scope.

FIG. 5A demonstrates a representative double immunostain for MC (anti-OX-7 antibody, brown) and BrdU (anti-BrdU antibody, black) on day five labeling proliferating MC. In FIG. 5B quantitation of BrdU positive, proliferating MC per glomerulus on day five is shown. MC-proliferation was also quantitated by double immunostaining for MC (anti-OX-7 antibody) and PCNA as a marker for cell proliferation as shown in FIG. 5C. Glomerular α-sm actin expression was examined as a marker for MC-activation using a semiquantitative scoring system as described in Methods as shown in FIG. 5D. The number of glomerular monocytes/macrophages was assessed by immunostaining for the marker protein ED-1 (E). FIG. 5F demonstrates the quantitation of the percentage of glomerular microaneurysm formation during the time course of disease. The star (*) marks significant differences (p<0.01) of the blocking peptide groups versus the control group.

DETAILED DESCRIPTION OF THE INVENTION

Figure 1:
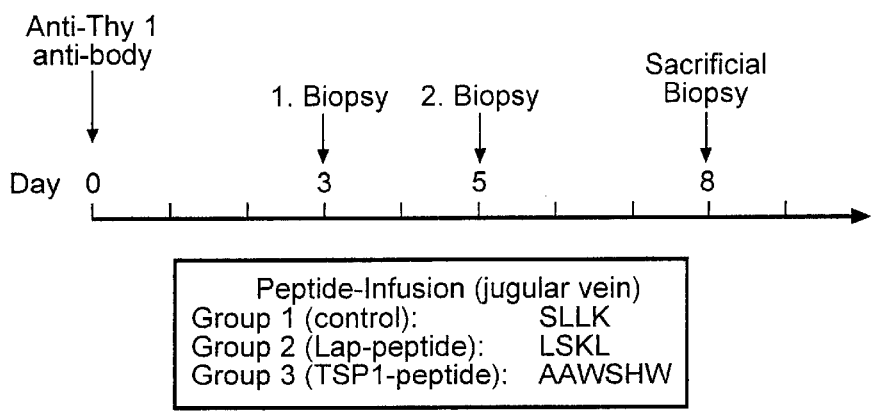
FIG. 1 is the schematic outline of the experimental design.

The present invention provides methods for treating kidney diseases, conditions, or disorders in a subject having a kidney disease, condition, or disorder. The method includes administering to the subject a pharmaceutically effective amount of a purified LAP peptide, a purified TSP peptide such as a TSP-1 type 1 repeat sequence and/or fragments thereof As defined herein, kidney disease, disorder, and/or condition includes any disease or condition of the kidney or renal system which can include glomerulonephritis, scarring glomerular disease, renal diseases having an inflammatory component, renal diseases having a glomerular extracellular matrix accumulation component, proteinuria, or microaneurysm formation. Further, the purified peptides can be administered to a subject in order to prevent the onset of a renal disease, disorder, or condition.

Preferably, the peptides of the present invention are LAP or TSP peptides and/or fragments thereof which are produced either synthetically or generated from native proteins which have been purified or by recombinant methods well known to those skilled in the art.

Broadly, the peptides useful for the method of the present invention are derived from the functional sequences of TSP. The purified peptides have between 4 and 30 amino acids, wherein the peptide comprises a subsequence W-$X_1$-$X_2$-W, wherein $X_1$ is an amino acid including Ser, Asn, or Gly; $X_2$ is an amino acid including Asp, Ser, His, or Pro; and W is Trp.

A preferred purified LAP peptide includes the peptide designated LSKL (SEQ ID NO:21) having the amino acid sequence Leu-Ser-Lys-Leu and a preferred purified TSP-1 type 1 repeat sequence includes the peptide designated AAWSHW (SEQ ID NO:22) having the amino acid sequence Ala-Ala-Trp-Ser-His-Trp.

The purified LAP peptide and/or the purified TSP peptide may contain partial or full retro-inverso modifications of the sequences or appropriate non-natural amino acids. The purified peptide can also be either partial and/or full retro-inverso peptide sequences. As used herein, the term "partial and full retro-inverso peptide sequences" means peptide sequences, determined to be inhibiting, which comprise some D-amino acids (partial) or consist entirely of D-amino acids (full), gem-diaminoalkyl residues, and alkylmalohyl residues. These can have modified or unmodified termini, or can include appropriate alkyl, acyl, or amine substitutions to modify the charge of the terminal amino acid residues.

These and other sequences and/or fragments derived from thrombospondin and LAP are determined to be effective in the treatment of kidney diseases/disorders by screening for inhibition of TGF-β activating function as described below in the examples.

The purified peptide can be conjugated to a water soluble polymer using standard protein conjugation protocols such as those described in Harlow and Lane *Antibodies, A Laboratory Manual*, Cold Springs Harbor Laboratory, Cold Spring Harbor, New York, N.Y. (1988). For example, suitable water soluble polymers include polysucrose, dextran, polyethylene glycol, and polyvinyl alcohol.

The term "subject" means all animals including humans. Examples of subjects include humans, cows, dogs, cats, goats, sheep, and pigs.

Abbreviations used in this paper: bw, body weight; BrdU, bromodeoxyuridine; DAB, diaminobenzidine; FGF, fibroblast growth factor; GEN, glomerular endothelial cell; PAN, aminonucleoside nephrosis; PHN, Passive Heyman Nephritis; MC, mesangial cell; PCNA, proliferation cell nuclear antigen; PDGF, platelet-derived growth factor; sm, smooth muscle; TGF-β, transforming growth factor beta; TSP, thrombospondin.

Those skilled in the art are easily able to identify subjects having or at potential risk for having kidney diseases and/or conditions, mesangial cell proliferation, glomerular endothelial cell proliferation, microaneurysm formation, and/or proteinuria and/or other conditions associated with renal dysfunction. For example, subjects who have mesangial proliferative glomerulonephritis or proteinuria.

A therapeutically effective amount is an amount of a purified peptide of the present invention, that when administered to a patient or subject, ameliorates a symptom of the disease, disorder, or condition.

The purified peptides of the present invention can be administered to a patient or subject either alone or as part of a pharmaceutical composition where the active ingredient includes a peptide as described above, a functional derivative or salt thereof, and a pharmaceutically acceptable carrier. As used herein, the term "functional derivative" refers to derivatives of free —OH, —SH, —$NH_2$ and —COOH groups, such as substitution of hydroxy groups by a halogen, e.g. iodo, and to ethers, esters, amides, and similar derivatives presenting chemical moieties not normally a part of the peptide. Examples of such substitutions are aminocaproyl, acetyl, and biotinyl.

The compositions can be administered to the patients or subjects either orally, rectally, parenterally (intravenously, intramuscularly, or subcutaneously), intracisternally, intravaginally, intraperitoneally, intravesically, locally (powders, ointments, or drops), or as a buccal or nasal spray.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the compositions can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present invention with suitable non-irritating excipients or carriers such as cocoa butter, polyethyleneglycol or a suppository wax, which are solid at ordinary temperatures but liquid at body temperature and therefore, melt in the rectum or vaginal cavity and release the active component.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

Pharmaceutically acceptable salts, esters, amides, and prodrugs can include those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively non-toxic, inorganic and organic acid addition salts of compounds of the present invention. These salts can be prepared in situ during the final isolation and purification of the protein or by separately reacting the purified protein in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, methane sulphonate and laurylsulphonate salts, and the like. These may include cations based on the alkalai and alkaline earth metals, such as sodium, lithium, potassium, calcium, magnesium, and the like, as well as non-toxic ammonium, quaternaly ammonium and amine cations including, but not limited to ammonium, tetramethylammonium, tetraethylammonium, methylamine, dimethylamine, trimethylamine, triethylamine, ethylamine, and the like. (See, for example, S. M. Berge, et al., "Pharmaceutical Salts," *J. Pharm. Sci.*, 1977; 66:1–19 which is incorporated herein by reference.)

Examples of pharmaceutically acceptable, non-toxic esters of the proteins of this invention include $C_1$–$C_6$ alkyl esters wherein the alkyl group is a straight or branched chain. Acceptable esters also include $C_5$–$C_7$ cycloalkyl esters as well as arylalkyl esters such as, but not limited to benzyl. $C_1$–$C_4$ alkyl esters are preferred. Esters of the compounds of the present invention may be prepared according to conventional methods.

Examples of pharmaceutically acceptable, non-toxic amides of the proteins of this invention include amides derived from ammonia, primary $C_1$–$C_6$ alkyl amines and secondary $C_1$–$C_6$ dialkyl amines wherein the alkyl groups are straight or branched chain. In the case of secondary amines the amine may also be in the form of a 5- or 6-membered heterocycle containing one nitrogen atom. Amides derived from ammonia, $C_1$–$C_3$ alkyl primary amines, and $C_1$–$C_2$ dialkyl secondary amines are preferred. Amides of the compounds of the invention may be prepared according to conventional methods.

The term "prodrug" refers to compounds that are rapidly transformed in vivo to yield the parent protein of the above amino acid sequence, for example, by hydrolysis in blood. A thorough discussion is provided in T. Higuchi and V. Stella, "Pro-drugs as Novel Delivery Systems," Vol. 14 of the A. C. S. Symposium Series, and in *Bioreversible Carriers in Drug Design*, ed. Edward B. Roche, American Pharmaceutical Association and Pergamon Press, 1987, both of which are incorporated herein by reference.

In addition, the peptides of the present invention can exist in unsolvated as well as solvated forms with pharmaceutically acceptable solvents such as water, ethanol, and the like. In general, the solvated forms are considered equivalent to the unsolvated forms for the purposes of the present invention.

The peptides of the present invention can be administered to a patient or subject at dosage levels in the range of about 35 mg to about 700 mg per day. For a normal human adult having a body weight of about 70 kilograms, a dosage in the range of about 0.5 mg to about 10 mg per kilogram of body weight per day is preferable. The specific dosage used, however, can vary. For example, the dosage can depend on a number of factors including the requirements of the patient, the severity of the condition being treated, and the pharmacological activity of the compound being used. The determination of optimum dosages for a particular patient is well known to those skilled in the art.

In addition, it is intended that the present invention cover peptides made either using standard organic synthetic techniques, including combinatorial chemistry or by biological methods, such as through metabolism or purification of native peptides.

Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are well known to those skilled in the art.

The examples presented below are intended to illustrate particular embodiments of the invention and are not intended to limit the scope of the specification, including the claims, in any way.

Methods

Experimental design. A scheme of the experimental protocol is shown in FIG. 1. Experimental mesangial proliferative glomerulonephritis was induced using the monoclonal mouse anti-Thy1 antibody OX-7. Peptides were continuously infused intravenously (i.v.) via jugular vein using osmotic minipumps starting sixteen hours after disease induction. The effects of the hexapeptide AAWSHW (SEQ ID NO:22) (that interferes with the TSP1-mature TGF-$\beta$ interaction) or the LSKL-peptide (SEQ ID NO:21) (that blocks the TSP1-LAP interaction) were compared to a control peptide (SLLK) in the anti-Thy1 model. Tissues from different time points (days three, five, eight) of this experiment were analyzed in regard to mesangiolysis, macrophage-influx, MC-proliferation, MC-activation, microaneurysm and matrix formation, GEN proliferation, TSP1, TGF-$\beta$1 and 2, as well as TGF-$\beta$RI and RII. Functional parameters such as blood pressure, proteinuria, and creatinine clearance were also determined. On day eight, glomerular secretion of active TGF-$\beta$ was determined in individual animals by incubating isolated glomeruli for twenty-four hours in DMEM and measuring TGF-$\beta$ activity in glomerular supernatants using the NRK-bioassay.

Animal model Experimental mesangial proliferative glomerulonephritis (anti-Thy1 model) was induced in Sprague Dawley rats (180–200 g; Charles River, Sulzfeld, Germany) by a single injection of 1 mg/kg of the mouse monoclonal anti-Thy1 antibody OX-7 (European Collection of Animal Cell Culture, Salisbury, England). In this animal model, complete anti-Thy1 antibody binding occurs within an hour (Johnson et al. (1991) *Am. J. Pathol.* 138 (2), 313–21). To avoid potential interference of the LAP-peptides with anti-Thy1 antibody binding and subsequent mesangiolysis, the peptide treatment was started sixteen hours after disease induction, when binding of the anti-Thy1 antibody to the mesangium and subsequent mesangiolysis had already occurred. The peptides used in this study were synthesized, purified, and analyzed as described elsewhere (Crawford et al. (1998) *Cell* 93, 1159–1170).

As shown in FIG. 1, six rats per group received treatment either with a control peptide SLLK (SEQ ID NO:47)-group 1, or with the LAP-peptide LSKL (SEQ ID NO:21)-group 2, or with the TSP-hexapeptide AAWSHW (SEQ ID NO:22)-group 3. Renal biopsies as described previously (Hugo et al. (1997) *J. Clin. Invest.* 100, 786–794) were performed on days three and five, and the experiment was finished on day eight. To determine DNA incorporation into proliferating cells, each animal was injected intravenously with BrdU (50 mg/kg bw) ninety minutes before the second survival biopsy was taken on day five (peak of MC proliferation). Renal biopsies were fixed in methyl Carnoy's, 10% formalin and/or OCT and snap frozen. A twenty-four hour urine collection for measurement of protein and creatinine was done from day seven to eight, when maximal proteinuria occurs in this model (unpublished observation). Blood pressure measurements were done twice before and twice after disease induction. In renal biopsies, the frequency of glomerular microaneurysms, the number of infiltrating macrophages, the number of proliferating MC, the expression of the contractile protein $\alpha$-sm actin as a marker of MC-activation, and the expression of TGF-$\beta$1, TGF-$\beta$2, TGF-$\beta$RI, TGF-$\beta$RII, TSP1, as well as of extracellular matrix proteins such as collagen I, collagen IV and fibronectin were determined. For TGF-$\beta$ activity measurements in individual animals on day eight, glomeruli were isolated by differential sieving (Johnson et al. (1991) *Am. J. Pathol.* 138 (2), 313–21) and counted using five aliquots. Glomerular isolates were discarded if purity was less than 95%. 8000 glomeruli/ml were incubated in DMEM at 37° C. After a twenty-four hour incubation period, glomerular supernatants were stored by –70° C. until TGF-$\beta$ activity measurements were done.

Peptide infusion. All peptides (at a concentration of 3.5 mg/ml) were continuously infused for seven days via a catheter in the right jugular vein using osmotic minipumps (Alzet Corp./Charles River, Sulzfeld, Germany). Implantation of minipumps (filing volume: 2 ml, delivery rate: 10 $\mu$l/h) and catheter was started sixteen hours after disease induction and was immediately followed by an additional i.v. injection of 3 mg peptide per kg body weight before rats recovered from anesthesia. Effective peptide-doses were extrapolated from pilot studies as described elsewhere (Hugo et al. (1999) in press *Kidney Int*).

Renal morphology and immunohistochemistry. Renal biopsies were fixed in methyl Carnoy's solution, embedded in paraffin, and cut into 5 $\mu$m sections for indirect immunoperoxidase staining as described elsewhere (Johnson et al. (1991) *Am. J. Pathol.* 138 (2), 313–21). Sections were also stained with the periodic acid Schiff reagent and counterstained with hematoxylin. For each biopsy, forty to seventy cortical glomerular cross-sections containing more than twenty discrete capillary segments each were evaluated in a blinded fashion in regard to the degree of mesangiolysis and relative frequency of microaneurysms (percentage). Mesangiolysis was graded semiquantitatively using the following scale: 0=no mesangiolysis, I=segmental and focal mesangiolysis (less than 25% of the glomeruli show partial dissolution of the mesangium), II=25%–50% of the glomeruli are affected, III=most (50%–75%) glomeruli show severe mesangiolysis, and IV=global mesangiolysis, where virtually all glomeruli show a complete dissolution of the mesangial areas. To determine general extracellular matrix formation, sections were also stained with the Masson's Trichrome (blue color) and semiquantitatively scored from 0 to 3 as follows: score 0=glomerulus without any blue staining, score 1=glomerulus with little blue staining, score 2=glomerulus with moderate blue staining, and score 3=glomerulus almost completely filled with blue staining.

The following antibodies were used in this study: A murine IgM monoclonal antibody (mAb) against the proliferating cell nuclear antigen (PCNA) (19A2, Coulter Immunology, Hialeah, Fla.); a murine IgG monoclonal antibody (mAb) against bromodeoxyuridine (BrdU); (Ed-1, a murine $IgG_1$ mAb to a cytoplasmic antigen present in monocytes, macrophages and dendritic cells (Serotec, Ltd., Oxford, United Kingdom); OX-7, a murine $IgG_1$ mAb specific for mesangial cells (Serotec); RECA-1, a murine $IgG_1$ mAb specific for detecting endothelial cells (Duijvestijn et al. (1992) *Lab. Invest.* 66 (4), 459–466) (Serotec); α-smooth muscle actin, a murine $IgG_2$ mAb specific for activated MC (Skalli et al. (1986) *J. Cell Biol.* 103 (6), 2787–2796) (Sigma Chemical Co., St. Louis, Mo.). Immunostaining for matrix proteins was conducted with polyclonal antibodies to collagen I, collagen IV (goat anti-human/bovine collagen IV, Southern Biotechnology Associates, Inc., Birmingham, Ala.), fibronectin (rabbit anti-rat fibronectin, Chemicon International, Inc., Temecula, Calif.), TGF-β1 (rabbit anti-human TGF-β1, Santa Cruz Biotechnology Inc., Santa Cruz, Calif.), TGF-β2 (rabbit anti-human TGF-β2, Santa Cruz Biotechnology Inc., Santa Cruz, Calif.), TGF-βR1 (rabbit anti-human TGF-β1, Santa Cruz Biotechnology Inc., Santa Cruz, Calif.), TGF-BR2 (rabbit anti-human TGF-βR2, Santa Cruz Biotechnology Inc., Santa Cruz, Calif.) and a murine $IgG_1$ mAb against TSP1 (Dunn, Labortechnik GmbH, Asbach, Germany). Negative controls for immunostaining included either deleting the primary antibody or substitution of the primary antibody with equivalent concentrations of an irrelevant murine monoclonal antibody or preimmune rabbit IgG. For each biopsy, forty to seventy glomerular cross-sections were evaluated in a blinded fashion. Glomerular expression of collagen I and IV, fibronectin, α-sm actin, TGF-β1, TGF-β2, and TSP1 was graded semiquantitatively (Hugo et al. (1995) *Kidney Int.* 48, 1846–1856) and reflected changes in the area and intensity of mesangial staining: 0: very weak or absent staining. 1+: weak staining with <25% of the glomerular tuft showing focally increased staining. 2+: 25–49% of the glomerular tuft with focally increased staining. 3+: 50–75% of the glomerular tuft demonstrating increased staining. 4+: >75% of the glomerular tuft stained strongly. It has been shown previously that this scoring system is reproducible between different observers and that the data obtained are highly correlated with those obtained by computerized morphometry (Kliem et al. (1996) *Kidney Int.* 49, 666–678; Hugo et al. (1996) *J. Clin. Invest.* 97 (11), 2499–2416). In addition, the average number of ED-1 positive macrophages per glomerular cross-section was determined.

Immunohistochemical double staining. To determine the number of proliferating MC, double immunostaining for PCNA or BrdU, both markers of cell proliferation, and for OX-7, a MC-specific marker was performed as described previously (Hugo et al. (1995) *Kidney Int.* 48, 1846–1856). Briefly, the first primary antibody (anti-OX-7) was incubated overnight at 4° C., followed sequentially by biotinylated rabbit anti-mouse $IgG_1$ serum (Zymed, San Francisco, Calif.), peroxidase conjugated Avidin D (Vector, Burlingame, Calif.), and color development with DAB without nickel chloride. Incubation in 3% $H_2O_2$/methanol for twenty minutes prevented any remaining peroxidase activity. Subsequently, the second primary antibody (anti-PCNA or anti-BrdU) was applied overnight at 4° C., followed by peroxidase conjugated rat anti-mouse IgM (anti-PCNA) or $IgG_2$ (anti-BrdU) antibody (Zymed) and DAB with nickel chloride as the second color reagent. The controls for all double staining procedures consisted of omitting either one of the secondary antibiotics and of omitting or replacing either one of the primary antibodies with an irrelevant mouse monoclonal antibody. The number of proliferating MC was evaluated by counting the number of cells that stained for both PCNA (black) and OX-7 (brown) or BrdU (black) and OX-7 (brown) as PCNA+/OX-7+ or BrdU+/RECA-1+ cells, respectively, and was expressed as mean±SD per glomerular cross-section.

TGF-β activity. Active TGF-β present in glomerular supernatants after a twenty-four hour incubation period was determined by colony formation by NRK cells in soft agar assays as described previously (Schultz-Cherry et al. (1994) *J. Biol. Chem.* 269, 26775–82). The number of colonies greater than 62 μm ($\geq$8–10 cells) in diameter were counted. Recombinant active TGF-β (R&D Systems, Minneapolis, Minn.) was used as a control. All experiments were done twice in triplicate.

Miscellaneous measurements. Urinary protein was measured using the BioRad Protein Assay (München, Germany) and BSA (Sigma, Deisenhofen, Germany) as a standard. Creatinine in serum or urine as well as blood urea nitrogen were measured using an autoanalyzer (Beckman Instruments GmbH, München, Germany). Systolic blood pressure was measured by tail plethysmography in conditioned, conscious rats (Pfeffer et al. (1971) *J. Lab. Clin. Med.* 78, 957–962).

Statistical analysis. All values are expressed as mean SD. Statistical significance (defined as $p<0.05$) was evaluated using the Student's t test or one way analysis of variance with modified t test using the Bonferroni method.

Results

Blocking peptides decreased activation of TGF-β in glomeruli from rats with anti-Thy1 disease.

Figure 2:
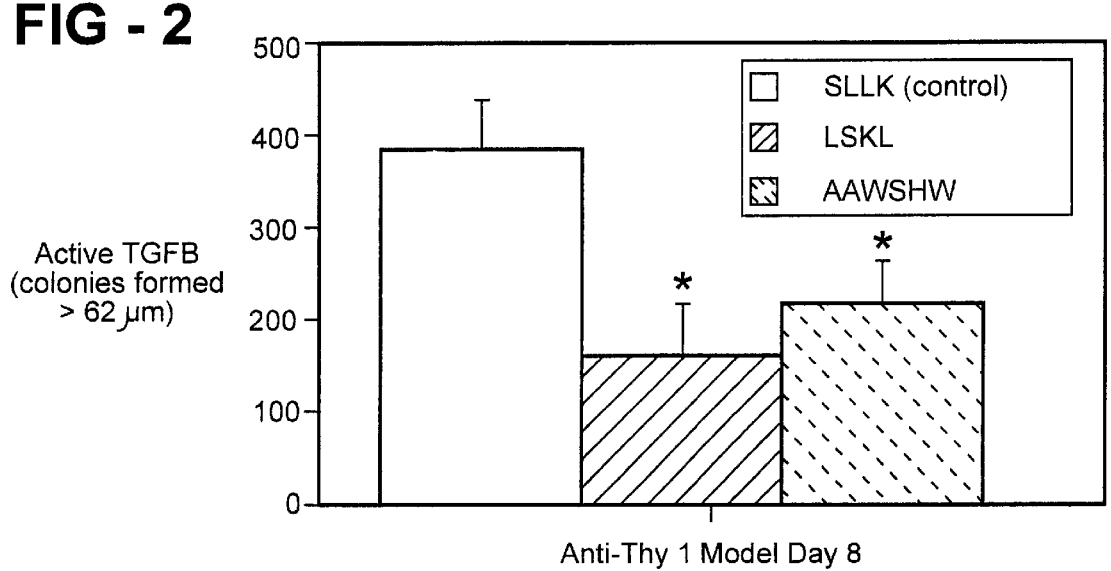
FIG. 2 is a chromatogram illustrating active TGF-β eight days after administration of test and control peptides. Blocking peptides (LSKL (SEQ ID NO:21) or AAWSHW (SEQ ID NO:22) decreased activation of TGF-β in glomeruli from rats with anti-Thy1 disease. TGF-β activity was measured in supernatants from day eight glomeruli using the NRK-bioassay (cell colonies≧62 μm or 8–10 cells were counted positive). Glomerular secretion of active TGF-β was markedly reduced in the LSKL-peptide (SEQ ID NO:21) and the AAWSHW-peptide (SEQ ID NO:22) treated group compared to the control (SLLK) (SEQ ID NO:47) peptide group. The star (*) marks significant differences (p<0.01) of the blocking peptide groups versus the control group.

If the ae novo expressed TSP1 is activating TGF-β in the anti-Thy1 model, then TGF-β activity in glomeruli from blocking peptide treated animals would be reduced. Since the amount of active TGF-β1 or TGF-β2 in glomeruli from individual rats was too small to be detectable by commercially available TGF-β assays (R&D Systems or Genzyme), TGF-β bioassays for measuring the active TGF-β fraction were applied. In the mink lung assay, TSP peptides have been shown to influence growth of the mink lung cells in a TGF-β independent fashion (Guo et al. (1997) *J. Peptide Res.* 50, 210–221 and this study). Since the NRK assay has been shown to be sensitive and specific for TGF-β activity measurements (Schultz-Cherry et al. (1993) *J. Cell Biol.* 122, 923–932; Schultz-Cherry et al. (1994) *J. Biol. Chem.* 269, 26775–82; Schultz-Cherry et al. (1995) *J. Biol. Chem.* 270, 7304–7310; Ribeiro et al. (1999) *J. Biol. Chem.* 274, 13586–13593; Crawford et al. (1998) *Cell* 93, 1159–1170), this well established assay was used to determine glomerular TGF-β activity of peptide-treated animals. Since detergents used for protein extraction of glomeruli interfere with the NRK-bioassay (this study) and may potentially lead to unspecific activation of TGF-β, isolated glomeruli from day eight animals were incubated for a twenty-four hour period in DMEM at 37° C. and the amount of secreted active TGF-β by these glomeruli was determined in the supernatant. As shown in Table 1 and FIG. 2, glomerular secretion of active TGF-β was markedly reduced in the LAP-peptide (LSKL (SEQ ID NO:21) treated group as well as in the TSP1-peptide (AAWSHW (SEQ ID NO:22) treated group compared to control peptide (SLLK (SEQ ID NO:47) treated rats (p<0.01).

Blocking peptides decreased glomerular extracellular matrix formation in rats with anti-Thy1 disease.

Figure 3A:
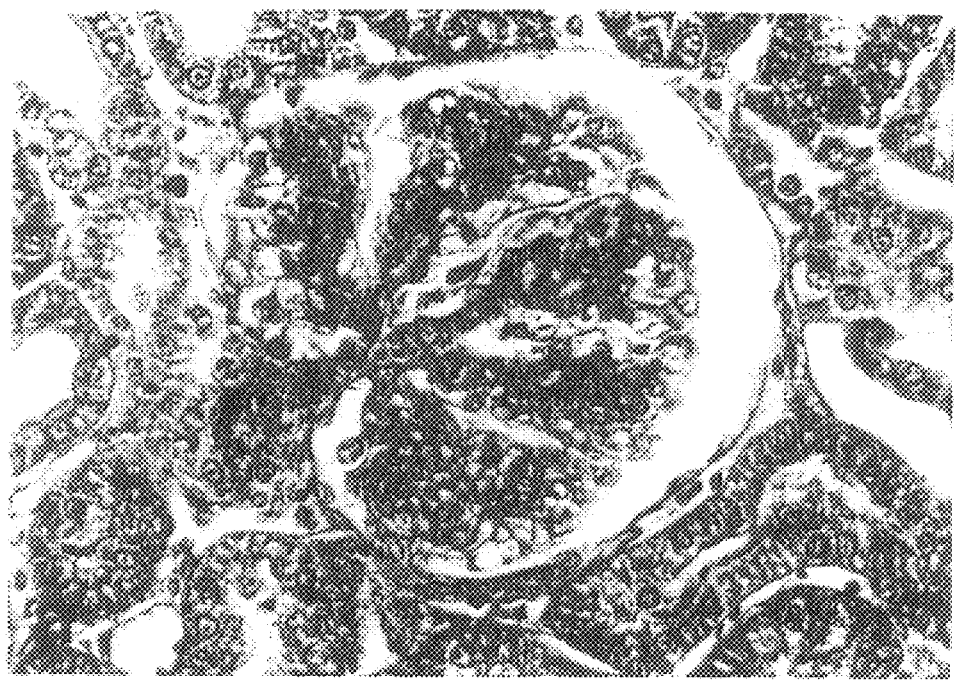
FIGS. 3A–F are photo-micrographs illustrating the effects of the peptides LSKL (SEQ ID NO:21) and AAWSHW (SEQ ID NO:22) in vivo in rats. Blocking peptides (LSKL (SEQ ID NO:21) or AAWSHW (SEQ ID NO:22) decreased glomerular extracellular matrix formation in rats with anti-Thy1 disease. Using Masson's Trichrome staining as a general indicator for fibrosis (as indicated by blue color) a marked reduction in blue staining was seen in day eight glomeruli from the blocking peptide treated groups (B) compared to the control group (A). In addition, immunostaining for collagen I (CID) or collagen IV (E/F) in brown was clearly reduced in day eight glomeruli from the peptide treated animals (DIF) compared to control animals (C/E).
Figure 3B:
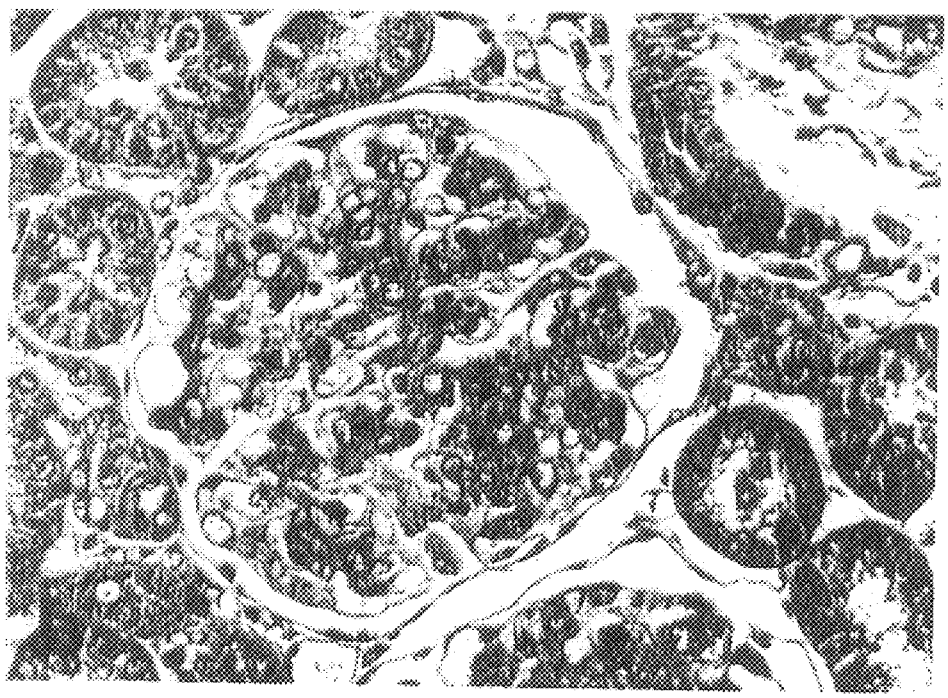
Figure 3C:
Figure 3D:
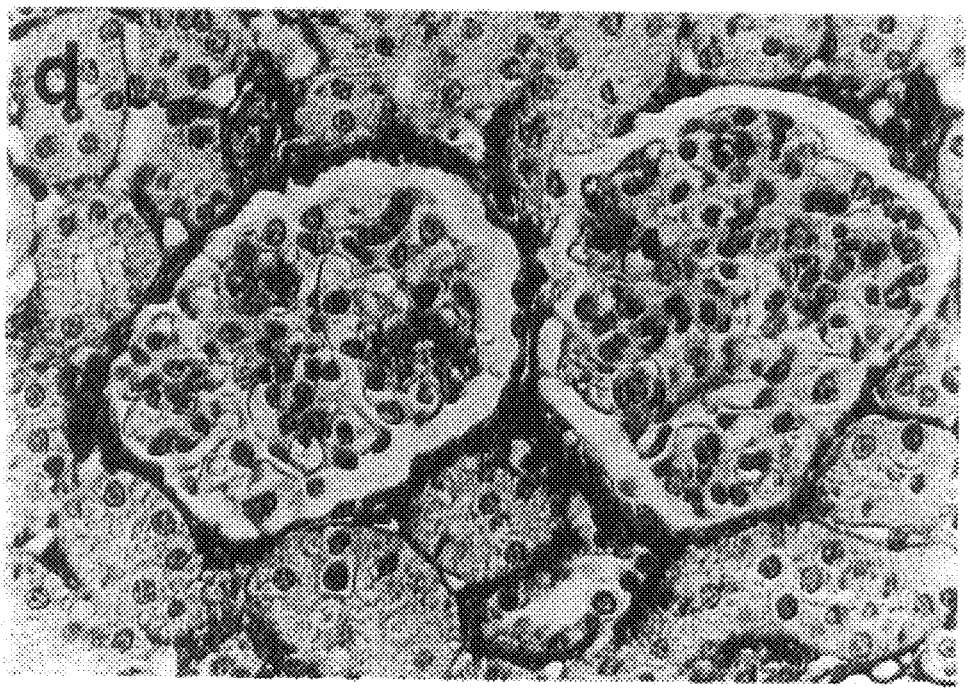
Figure 3E:
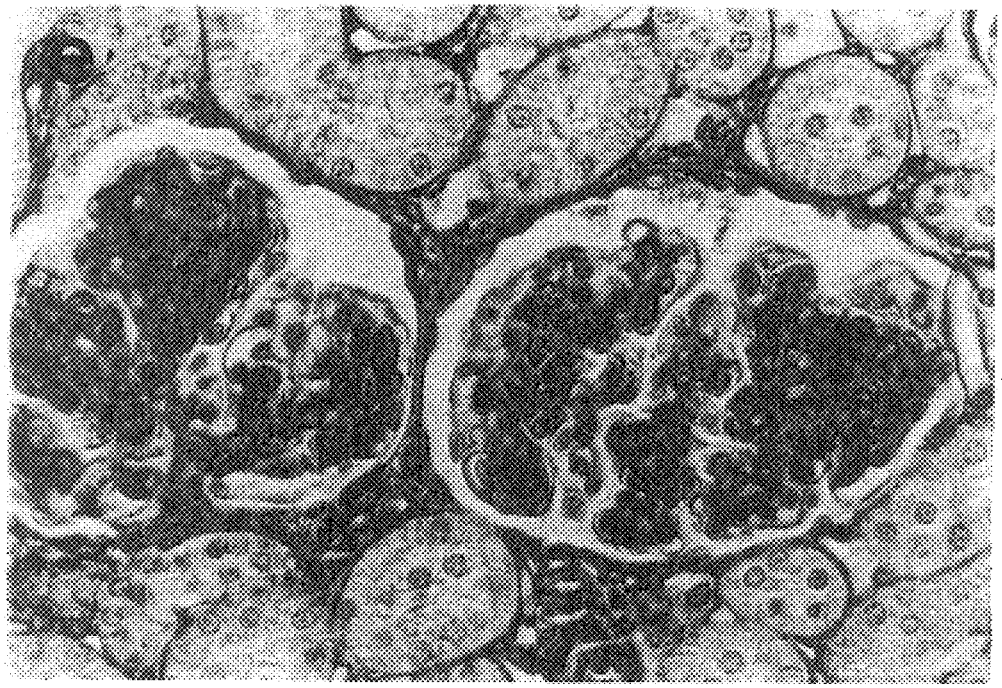
Figure 3F:
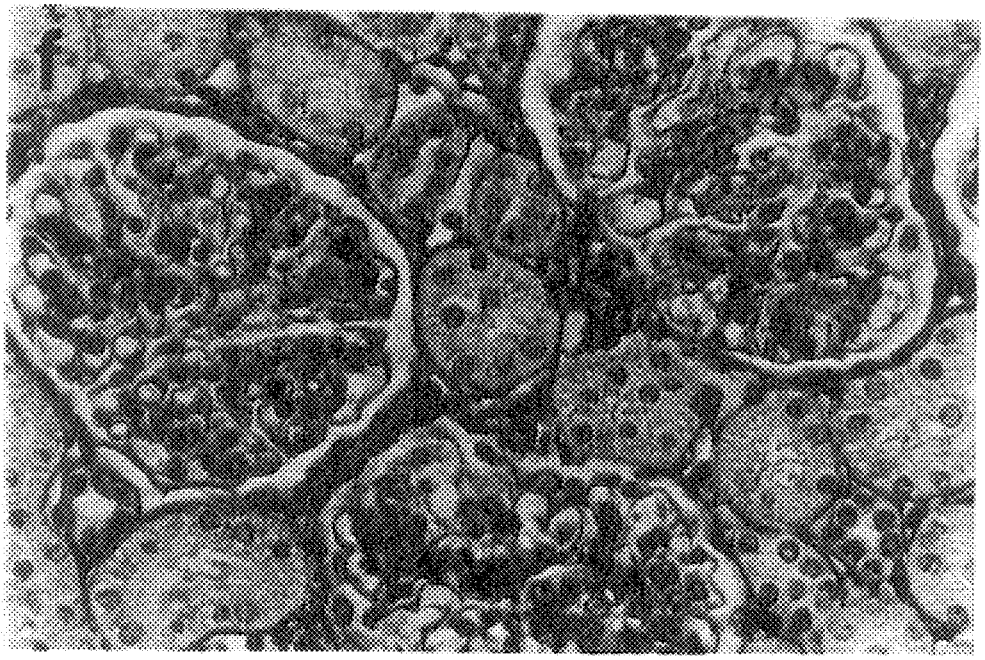
Figure 4A:
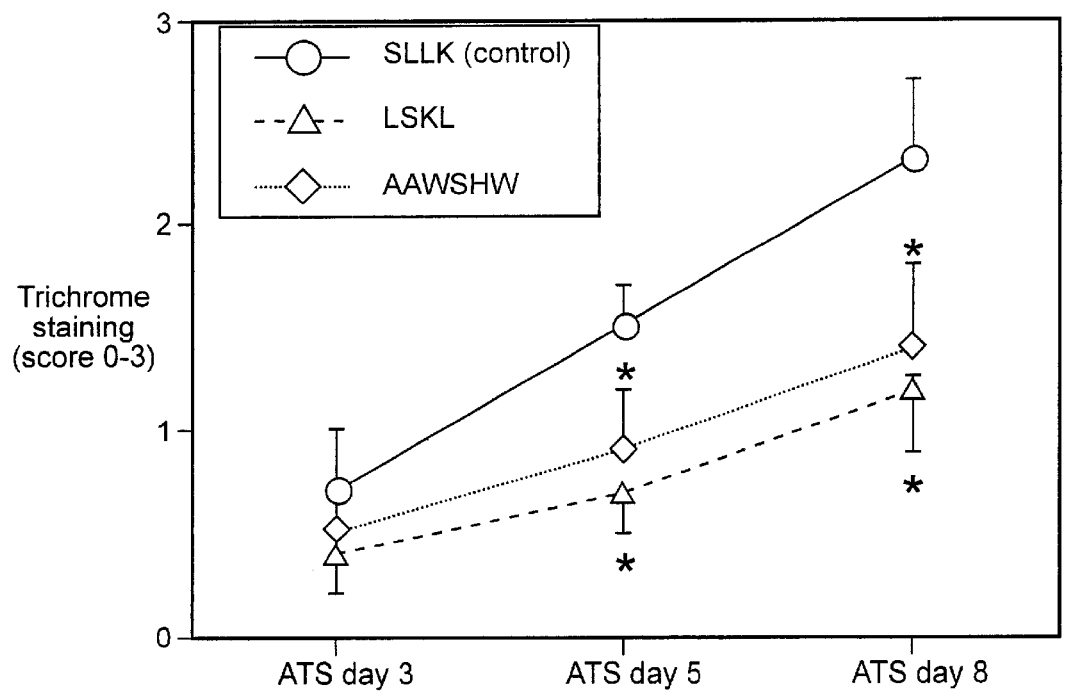
FIGS. 4A–D are graphs of test and control peptides scored over time for their ability to decrease glomerular extracellular matrix formation. Blocking peptides (LSKL (SEQ ID NO:21) or AAWSHW (SEQ ID NO:22) decreased glomerular extracellular matrix formation in rats with anti-Thy1 disease. Using a semiquantitative scoring system as described in Methods, the Masson's Trichrome staining as well as immunostainings for collagen I, IV, and fibronectin were evaluated. Blocking peptide treatment significantly reduced extracellular matrix formation as determined by the Trichrome (A), collagen I (B), IV (C), and fibronectin (D) staining during the time course of the anti-Thy1 model. The star (*) marks significant differences (p<0.01) of the blocking peptide groups versus the control group.
Figure 4B:
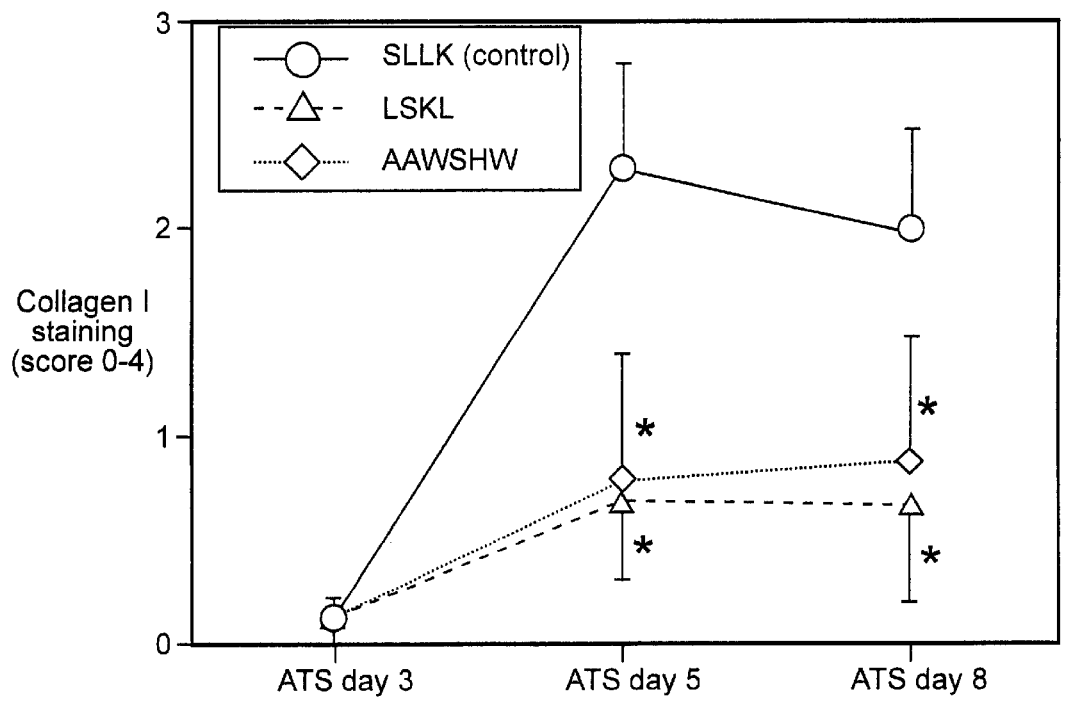
Figure 4C:
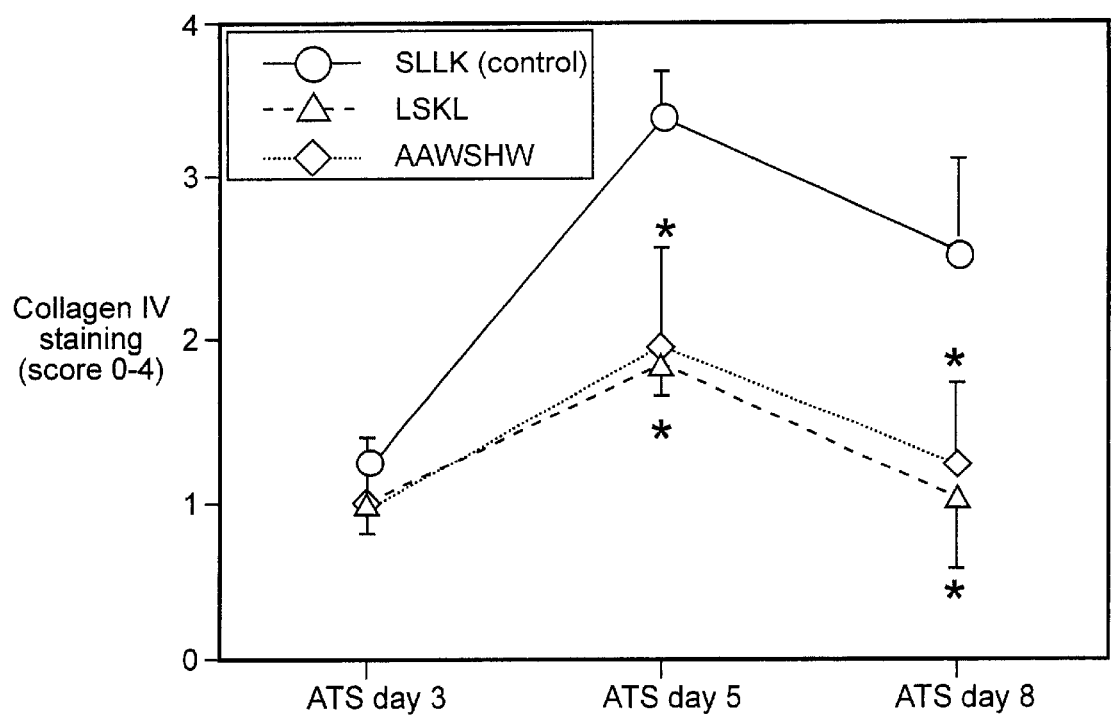
Figure 4D:
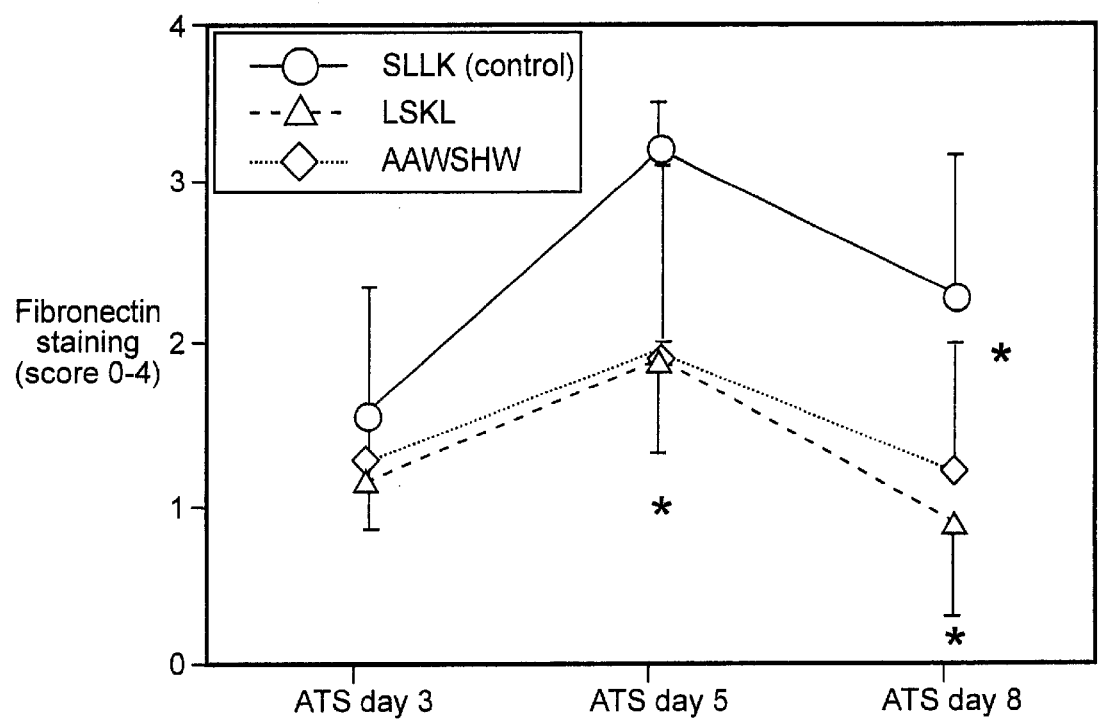
Figure 5A:
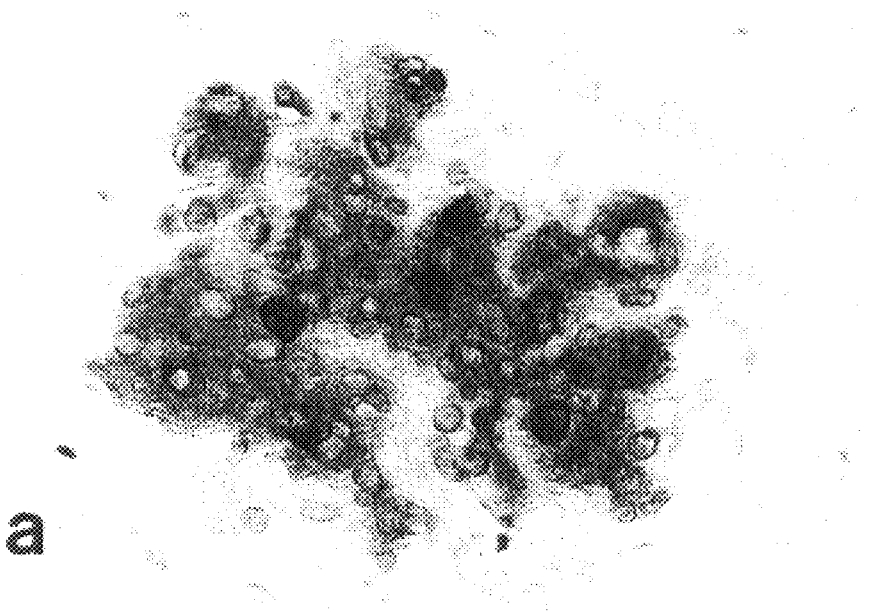
FIGS. 5A–F—Blocking peptides did not affect glomerular MC-proliferation, -activation, influx of monocytes/macrophages, or microaneurysm formation.
Figure 5B:
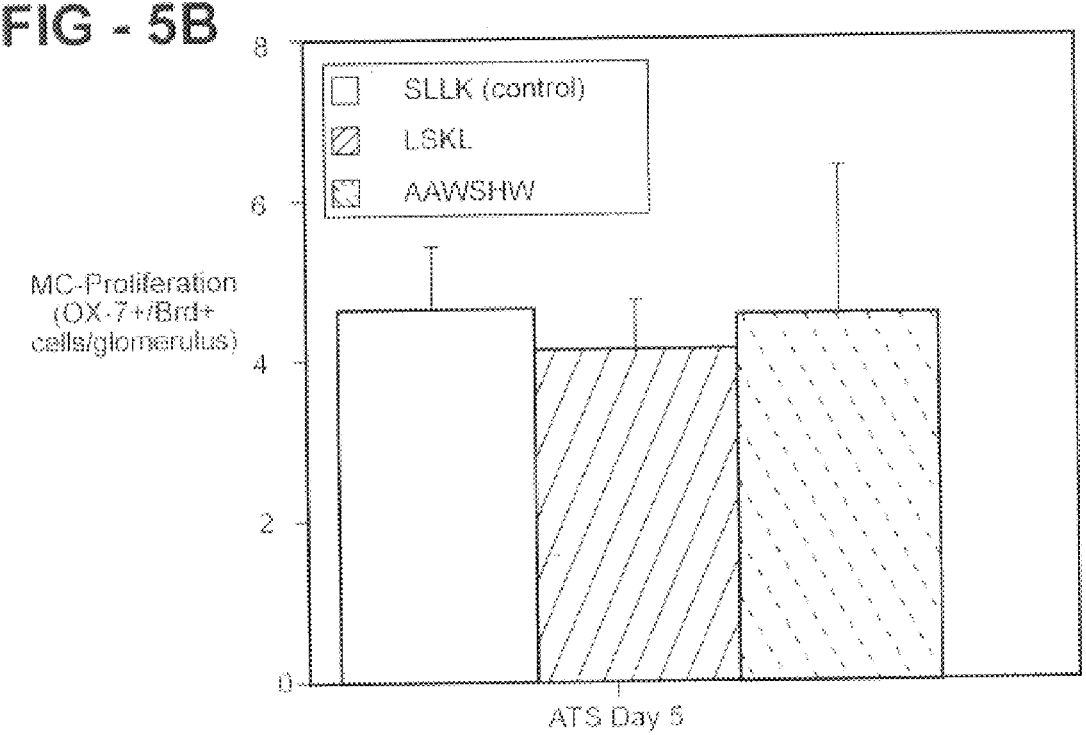
Figure 5C:
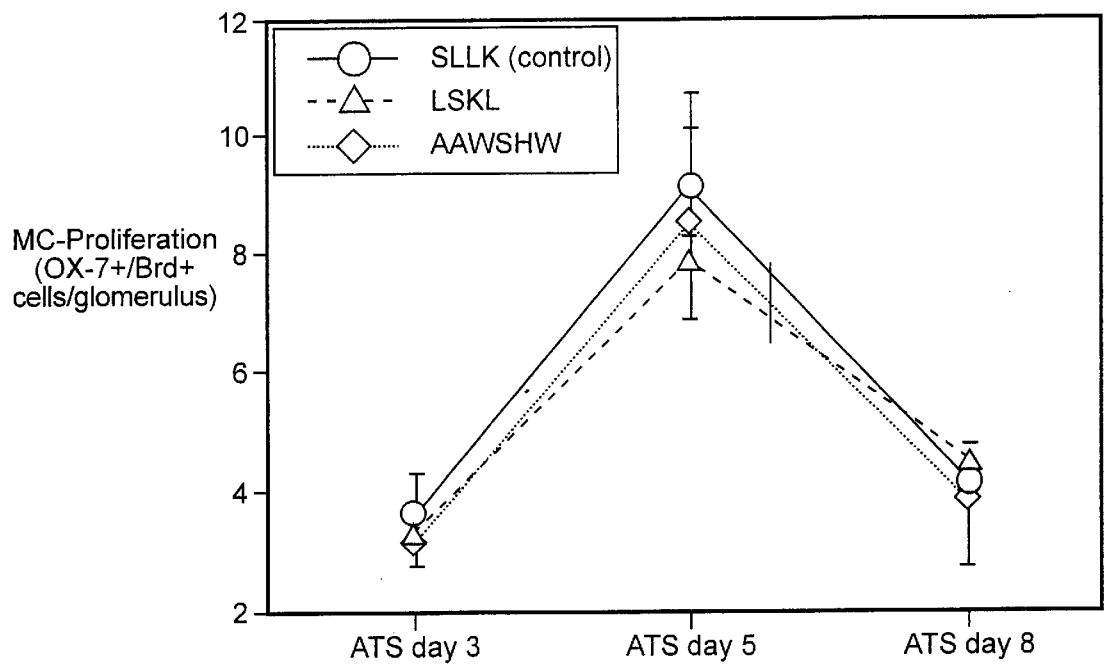
Figure 5D:
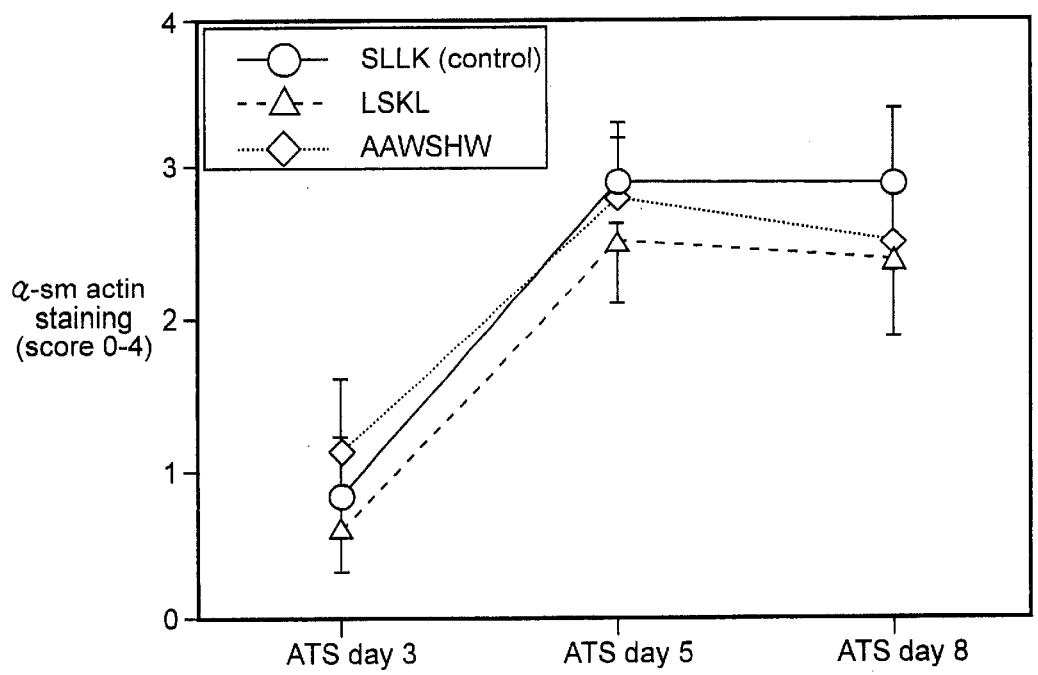
Figure 5E:
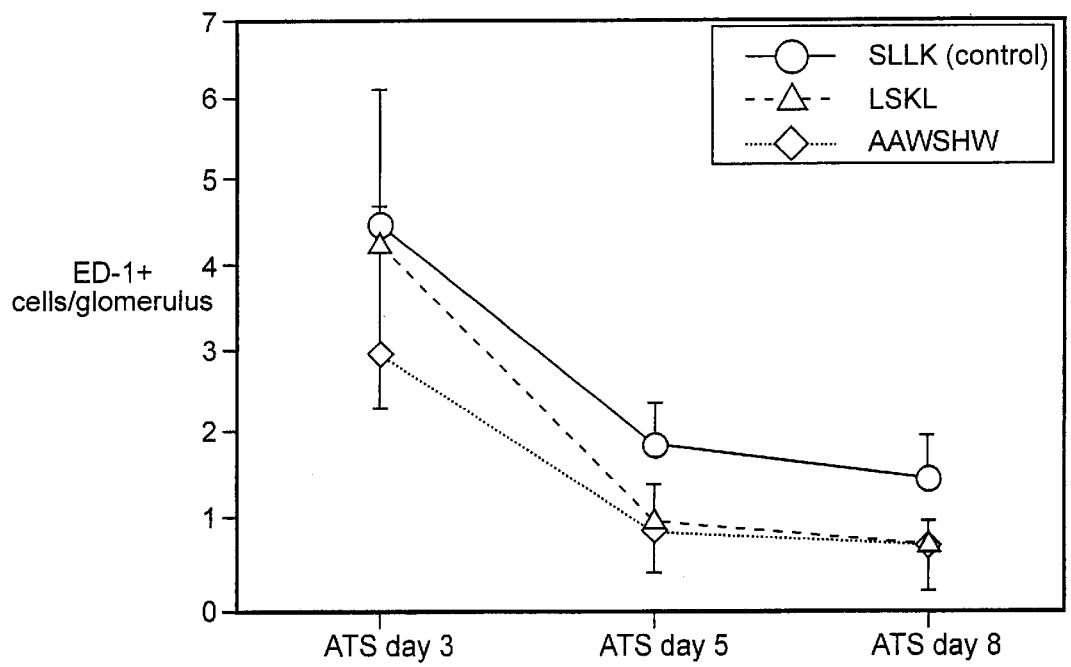
Figure 5F:
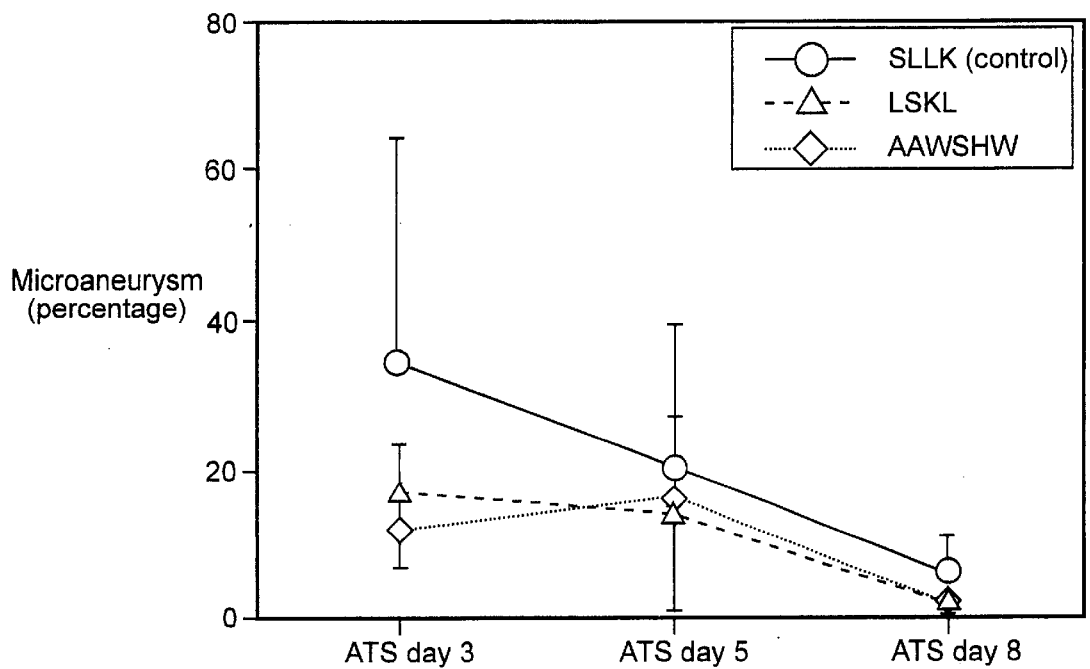

Since TGF-β has been demonstrated to cause excess formation of extracellular matrix in the anti-Thy1 model (Border et al. (1990) Nature 346, 371–374; Border et al. (1992) Nature 360, 361–364; Akaki et al. (1996) Kidney Int. 50, 148–155; Isaka et al. (1996) Nat. Med. 2, 418–423), we evaluated if suppression of TGF-β activity by blocking peptides is accompanied by decreased matrix formation. Using Masson's Trichrome staining as a general indicator for fibrosis (here blue color), no blue staining is detected in normal glomeruli. In the anti-Thy1 model, diseased glomeruli on day three or day five exhibit no or very little blue staining, while a marked increase in blue staining was seen on day eight (see FIG. 3A). Treatment with either the LAP-peptide (LSKL (SEQ ID NO:21), group 2) or the TSP1-peptide (AAWSHW (SEQ ID NO:22), group 3) markedly suppressed extracellular matrix formation on day eight as determined by Trichrome staining (see Table 1, FIGS. 3B and 4). This result was confirmed by examining specific typical extracellular matrix proteins such as collagen I and IV as well as fibronectin during the time course of anti-Thy1 disease using immunohistochemistry. In the anti-Thy1 model, the typical interstitial protein collagen I is transiently expressed de novo by glomerular MC starting on day three and peaking on day five, while the constitutively expressed MC-proteins collagen IV and fibronectin are also markedly increased in parallel to collagen I. Treatment with either the LAP-peptide (LSKL (SEQ ID NO:21), group 2) or the TSP1-peptide (AAWSHW (SEQ ID NO:22), group 3) reduced glomerular accumulation of all three extracellular matrix proteins as determined by immunohistochemistry (see Table 1, FIGS. 3C–F). Evaluation of extracellular matrix accumulation using a semiquantitative scoring system demonstrated that the changes induced by the treatment of either the LSKL (SEQ ID NO:21) or the AAWSHW (SEQ ID NO:22) peptide were significant compared to the control peptide and that in general the LSKL (SEQ ID NO:21) peptide treatment was slightly superior to the AAWSHW (SEQ ID NO:22) peptide in suppressing matrix accumulation as well as TGF-β activity (see Table 1, FIGS. 2–4).

Blocking peptides did not affect the glomerular amount of TGF-β1 or -β2, TGFβ-RI or -RII, or TSP1 in rats with anti-Thy1 disease.

To determine whether potential feedback mechanisms between TSP1, active TGF-β, and TGF-β receptors were altered by the infusion of blocking peptides, the amount of glomerular TSP1, TGF-β1 and -β2, as well as TGF-βRI and -RII was evaluated using an immunostaining score as described in Methods. Although there was a tendency to a reduced expression of TSP1, TGF-β1, TGF-β2, TGF-βRI, or TGF-βRII, these changes were not significant compared to the control group (see Table 1).

Blocking peptides did not affect glomerular MC-proliferation or -activation or influx or macrophages in rats with anti-Thy1 disease.

1. MC-proliferation. Since TGF-β has been shown to inhibit MC-proliferation in vitro (Schöcklmann et al. (1997) Kidney Int. 51, 1228–1236) we also examined if a reduced TGF-β activity in blocking-peptide treated animals is accompanied by an increased proliferative response of MC.

To determine MC-proliferation, double immunostaining for PCNA (a marker of proliferation) and OX-7 (a marker of MC) was performed during the time course of disease. As previously described (Hugo et al. (1995) Kidney Int. 48, 1846–1856; Hugo et al. (1997) J. Clin. Invest. 100, 786–794; Hugo et al. (1999) in press Kidney Int.), MC proliferation was already increased on day three, peaked on day five, and ceased on day eight. Despite alteration of TGF-β activity and matrix formation, the proliferative response of the MC was unchanged by any peptide-treatment in the anti-Thy1 model (see Table 1, FIG. 5). This result was confirmed by double staining on day five biopsies for MC and for BrdU indicating the number of MC that have incorporated the injected BrdU during the phase of DNA-synthesis (OX-7+/BrdU+ cells) (see Table 1, FIG. 5).

2. MC-activation. De novo expression of α-sm-actin during the time course of mesangial proliferative glomerulonephritis is considered to be a specific marker of MC activation (Johnson et al. (1991) J. Clin. Invest. 87 (3), 847–58). Treatment with either the LSKL- or the AAWSHW-peptide did not significantly alter this phenotypical response of the injured MC (see Table 1, FIG. 5).

3. Influx of monocytes/macrophages. Since TGF-β has been shown to be chemotactic for monocytes/macrophages in vitro (Wahl (1992) J. Clin. Immunol. 12, 61–74), the number of ED-1 positive monocytes/macrophages per glomerular cross-section was evaluated by immunostaining and did not differ in any group during this experiment (see Table 1, FIG. 5).

Blocking peptides did not affect mesangiolysis, microaneurysm formation, or GEN-proliferation in rats with anti-Thy1 disease.

To assure that disease induction was equal in all groups, peptide treatment was started sixteen hours after anti-Thy1 antibody injection. In addition, mesangiolysis scores on day three in the LSKL group (2.56±0.3), or AAWSHW group (2.5±0.4) were unchanged compared to the control group (2.7±0.5). Microaneurysm formation in the anti-Thy1 model relates to GEN stretching, denudation and subsequent injury, and an angiogenesis-like process including GEN-proliferation is required for its repair (Iruela-Arispe et al. (1995) Am. J. Path. 147, 1715–1727). Although microaneurysm formation tended to be decreased in the blocking peptide groups, this difference was not significant (see Table 1, FIG. 5). In fact, the elevated percentage of microaneurysm formation in the SLLK control group was mainly due to one animal that showed almost 100% microaneurysms on day three. Glomerular GEN-proliferation on day three (as assessed by double staining for RECA-1 and PCNA) was unchanged in the LSKL (2.0±0.5) or AAWSHW group (1.8±0.6) compared to the control SLLK group (2.235 0.4).

Functional parameters: LSKL-peptide infusion decreased proteinuria in experimental glomerulonephritis.

Proteinuria, a hallmark of severity of kidney disease, is maximally increased around day seven to eight in the OX-7 antibody-induced anti-Thy1 model (unpublished observation). Either one of the blocking peptides reduced twenty-four hour proteinuria on days seven to eight compared to control animals, while the effect of the LSKL (SEQ ID NO:21) peptide was more dramatic and did reach significant values (SLLK (SEQ ID NO:47) control 83±40 mg/twenty-four hours, LSKL (SEQ ID NO:21) 24±20 mg/twenty-four hours*, AAWSHW (SEQ ID NO:22) 51±50 mg/twenty-four hours; *p<0.01 versus control). Creatinine clearance on day eight as a measurement of kidney function tended to be improved by infusion of either one of the blocking peptides, but did not reach significant values (SLLK (SEQ ID NO:47) control 1.52±0.2 ml/min, LSKL (SEQ ID NO:21) 1.78±0.3 mi/mn, AAWSHW (SEQ ID NO:22) 1.87±0.2 ml/min). Blood urea nitrogen was also unchanged by the peptide treatment (SLLK control 33.2±12.7 mg/ml, LSKL (SEQ. ID NO:21) 33.2±9.4 mg/ml, AAWSHW (SEQ ID NO:22) 23.6±7.1 mg/ml). In addition, none of the blocking peptides affected systolic blood pressure levels in diseased or healthy rats (not shown).

Discussion

Overproduction of TGF-β in response to injury is thought to cause tissue fibrosis in many different inflammatory disease processes. This concept is particularly well established in experimental glomerular disease (Border et al. (1994) N. Engl. J. Med. 331, 1286–1292). Most cells secrete TGF-β as a latent procytokine complex that requires extracellular activation before it can interact with its receptors (Harpel et al. (1992) Prog. Growth Factor Res. 4, 321–335). Despite great interest in therapeutic anti-TGF-β strategies to treat fibrotic disease, the mechanism of TGF-β activation in an inflammatory process in vivo is still unknown. The data presented above demonstrate that TSP1 is an important endogenous activator of TGF-β in inflammatory kidney disease. Continuous systemic administration of synthetic peptides inhibited glomerular TGF-β activation by TSP1 in rats with experimental mesangial proliferative glomerulonephritis and provided a remarkable reduction of glomerular extracellular matrix accumulation and proteinuria, while MC-proliferation, microaneurysm formation, or influx of monocytes/macrophages was unaffected.

In the anti-Thy1 model of mesangial proliferative glomerulonephritis, a marked transient de novo expression of the matricellular protein TSP1 by MC (peak on day five) was regulated by FGF-2 and PDGF (Hugo et al. (1995) Kidney Int. 48, 1846–1856) and coincided with the upregulation of TGF-β (Okuda et al. (1990) J. Clin. Invest. 86, 453–462). The data set forth herein demonstrate TSP1 as a major endogenous activator of TGF-β in inflammatory kidney disease and identify a potential therapy for disorders with overproduction (-activation) of TGF-β. Continuous systemic infusion of the peptide (AAWSHW (SEQ ID NO:22) that inhibits interaction of TSP1 with the mature TGF-β protein (within the TGF-β procytokine-complex) (Schultz-Cherry et al. (1995) J. Biol. Chem. 270, 7304–7310) or infusion of the peptide (LSKL (SEQ ID NO:21) that blocks interaction of TSP1 with the LAP of TGF-β was able to reduce the amount of active TGF-β secreted by glomeruli on day eight of disease (Ribeiro et al. (1999) J. Biol. Chem. 274, 13586–13593). This inhibition of glomerular TGF-β activation was accompanied by a marked suppression of the glomerular matrix excess on days five and eight as assessed by Trichrome staining and specific stainings for collagen I, IV, and fibronectin. The LSKL-peptide (SEQ ID NO:21) was superior in inhibiting activation of TGF-β and extracellular matrix accumulation. In addition, the LSKL (SEQ ID NO:21) peptide treatment also significantly reduced proteinuria, a hallmark of severity of kidney disease, while the reduction of proteinuria by the AAWSHW (SEQ ID NO:22) peptide did not reach significant values. Both therapeutic effects of the peptide treatment, suppression of extracellular matrix accumulation and proteinuria, are in good agreement with previous studies antagonizing TGF-β by antibodies, decorin-injections, or gene therapy (Border et al. (1990) Nature 346, 371–374; Border et al. (1992) Nature 360, 361–364; Akaki et al. (1996) Kidney Int. 50, 148–155; Isaka et al. (1996) Nat. Med. 2, 418–423; Kopp et al. (1996) Lab. Invest. 74, 991–1003; Isaka et al. (1993) J. Clin. Invest. 92, 2597–2601).

Excessive proliferation of mesangial cells is characteristic for many glomerular diseases and is frequently linked to extracellular matrix accumulation (Johnson (1994) Kidney Int. 45 (6), 1769–82). Despite reducing TGF-β activity, blocking peptide treatment did not affect MC proliferation as assessed by double immunostaining for MC (OX-7) and PCNA or BrdU as markers of proliferation. Although TGF-β inhibits cell proliferation in vitro in different cell types including MC (Schöcklmann et al. (1997) Kidney Int. 51, 1228–1236; Sharma et al. (1994) Am. J. Physiol. 35, F829–F842), the pathophysiological role of TGF-β in regard to mesangial cell proliferation in experimental glomerulonephritis has not been well examined and is still controversely discussed. In vivo transfection of the TGF-β1 gene into glomeruli of normal rats induced glomerular hypercellularity (Isaka et al. (1993) J. Clin. Invest. 92, 2597–2601), while transfer of the TGF-β1 gene into nephritic glomeruli during anti-Thy1 disease (Kitamura et al. (1995) Kidney Int. 48, 1747–1757) led to a reduced glomerular mitogenic activity as determined by 3H-thymidine incorporation. Both studies did not determine specifically the number of proliferating MC versus endothelial or infiltrating cells. Studies in the anti-Thy1 model inhibiting TGF-β1 activity by a polyclonal anti-TGF-β1 antibody or TGF-β1–3 activity by decorin-treatment focused on matrix accumulation and did not evaluate glomerular cell or MC proliferation (Border et al. (1990) Nature 346, 371–374; Border et al. (1992) Nature 360, 361–364; Isaka et al. (1996) Nat. Med. 2, 418–423). Inhibition of glomerular TGF-β1 expression by antisense oligonucleotides did not affect glomerular cell counts in the anti-Thy1 model on day nine, but MC proliferation was not separately examined (Akaki et al. (1996) Kidney Int. 50, 148–155). Taken together, active TGF-β1 and in particular the TSP1-mediated fraction of active TGF-β does not appear to be a critical player in inhibiting MC proliferation in experimental mesangial proliferative glomerulonephritis.

Influx of monocytes/macrophages into the glomerulus is also a characteristic feature of inflammatory glomerular disease. In vivo and in vitro studies have shown that TGF-β1 can be chemotactic for mononuclear cells as well as it can reduce macrophage adhesiveness, which potentially leads to deactivation and/or increased clearance from inflammatory sites (Suito et al. (1996) Kidney Int. 50,445–452). Blocking peptide treatment in this study did not affect macrophage accumulation in glomeruli between day three and day eight in the anti-Thy1 model. To avoid any potential effect on disease induction, peptide treatment was started sixteen hours after the anti-Thy1 antibody injection briefly before the time of maximal glomerular macrophage accumulation (day one to two, unpublished observation). Although it seems unlikely, we cannot completely exclude a role for TSP1/TGF-β in influencing macrophage influx or clearance during the very early phase of anti-Thy1 disease, when platelets are the only source of glomerular TSP1 (and are still detectable for the first three to five days).

Since TSP1 is able to activate both TGF-β1 and TGF-β2 in an identical manner that canbe blocked by either peptide (Ribeiro et al. (1999) J. Biol. Chem. 274, 13586–13593), and since glomerular TGF-β1 and TGF-β2 are increased in the anti-Thy1 model (see Table 1), it cannot be excluded by this study that the effect of the blocking peptide treatment is due to inactivation of both TGF-β1 and TGF-β2. Nevertheless, the therapeutic effect seen by TGF-β1 inhibition using polyclonal antibodies or antisense oligonucleotides was very similar to the effects of the blocking peptide treatment in this study (Border et al. (1990) *Nature* 346, 371–374; Akaki et al. (1996) *Kidney Int.* 50, 148–155).

Comparing the degree of glomerular TGF-β activation and extracellular matrix formation in blocking peptide treated disease animals to normal rats, our data suggest that TSP1 is a major activator of TGF-β in disease, but does not exclude participation of other activators of TGF-β or direct secretion of the active cytokine by glomerular cells. The incomplete inhibition of TGF-β activation is consistent with the role of TSP1 in regard to TGF-β activation during mouse post-natal development, and may prove to be a great advantage as a potential anti-TGF-β strategy in inflammatory disease as supported by studies comparing the TSP1 and TGF-β1 null mice during mouse post-natal development (Crawford et al. (1998) *Cell* 93, 1159–1170). Pathological changes in several organs of the TSP1 null pups are due to a reduction, but not complete absence of TGF-β activity, and the very severe phenotype of the TGF-β1 null mice characterized by early death and a generalized excessive inflammatory response (due to a multifactorial dysregulation of the immune system, Shull et al. (1992) *Nature* 359, 693–699) are not duplicated by the TSP1 null mice (Crawford et al. (1998) *Cell* 93, 1159–1170). In addition, mice with deletion of one allele of TGF-β1 have generally reduced TGF-β1 serum and tissue levels. Reduced TGF-β1 levels in these mice are associated with increased cell turnover and susceptibility to tumorigenesis in liver and lung (Bottinger et al., personal communication), which has not been described for the TSP1 null mice suggesting that other mechanisms of TGF-β activation are operative in these conditions. Therefore, therapeutic strategies focusing on nonspecific, systemic blockage of TGF-β ligand-receptor interactions may have problematic side effects considering the complex function of TGF-β in vivo. In contrast, targeting TSP-1 mediated activation of TGF-β as a therapeutic intervention for fibrotic kidney disease may have great promise, because alternate activation pathways of TGF-β are not affected. Specificity of this treatment relates to the fact that TSP1-mediated TGF-β activation requires a direct interaction of secreted TSP1 and TGF-β in a complex extracellular neighborhood and that TSP 1 is tightly regulated in disease. In most in vitro systems or in normal tissues, very little TGF-β is present in its biologically active form. In contrast, the latent TGF-β procytokine-complexes and the TGF-β receptors are highly and widely expressed in most tissues (Barcellos-Hoff (1996) *J. Mam. Gland. Biol. Neoplasia* 1, 351–361). In this context, it is interesting that in vivo gene transfer of the constitutively active TGF-β gene into the lung of rats caused extensive fibrosis, while overexpression of the latent TGF-β1 transgene did not (Sime et al. (1997) *J. Clin. Invest.* 100, 768–776). Although TGF-β is also upregulated in many disease processes including the anti-Thy1 model, the studies described above and the data from this study suggest that regulation of TGF-β activation and therefore, of a TGF-β activator, is critical to its profibrotic action. TSP1 fits into the role of a tightly regulated activator of TGF-β that is induced by other cytokines such as PDGF and FGF-2, as well as potentially TGF-β in response to injury. In the normal rat glomerulus, TSP1 expression is below detection level. In anti-Thy1 disease, glomerular TSP1 and mRNA and protein is transiently, dramatically upregulated by PDGF and FGF-2 (Hugo et al. (1995) *Kidney Int.* 48, 1846–1856) in parallel to TGF-β. Although blocking peptide treatment decreased TGF-β1 and TGF-β2 as well as TSP1 staining in the anti-Thy1 model to some extent, this difference was statistically not significant and suggests that a positive feedback loop between TSP1 and TGF-β may participate, but is not critical in the anti-Thy1 model. In addition, peptide treatment did not significantly affect glomerular TGF-βRI or II regulation during disease.

Just as these peptides will not affect activation of TGF-β by other mechanisms, they should also not influence other functions of TSP1. TSP1 is one of the most potent natural inhibitors of angiogenesis and its expression in the anti-Thy1 model coincides with a decrease of GEN proliferation (Hugo et al. (1995) *Kidney Int.* 48, 1846–1856; Iruela-Arispe et al. (1995)*Am. J. Path.* 147, 1715–1727). Although a role for TSP1 in suppressing GEN proliferation in this model has not been established yet, infusion of antiangiogenic peptides from the type I repeat of the TSP1 molecule markedly suppressed GEN proliferation and subsequent microaneurysm formation (Hugo et al. (1999) in press *Kidney Int.*), while TGF-β blocking peptide infusion in this study did not influence GEN proliferation or microaneurysm formation.

Studies have demonstrated a link of local TSP1 and TGF-β expression/activity with the development of subsequent fibrosis in several experimental kidney disease models (anti-Thy1 model, Passive Heyman Nephritis (PHN), aminonucleoside nephrosis (PAN)) (Hugo et al. (1998) *Kidney Int.* 53,302–311). In many injury models in different organs as well as in human kidney disease (Sharma et al. (1994) *Am. J. Physiol.* 35, F829–F842; McGregor et al. (1994) *Am. J. Pathol* 144, 1281–1287), TSP1 expression is consistent with a role of TSP1 in mediating TGF-β activation and possibly fibrosis. Future studies in different organ systems as well as in human disease may have to prove whether TSP1 leads to activation of TGF-β in very limited situations or whether this interaction is critical for many different disease processes where fibrosis is an important factor.

In conclusion, the studies described above identify TSP1 as a major activator of TGF-β in an inflammatory glomerulonephritis model in the rat. This activator of TGF-β is tightly regulated by cytokines such as PDGF, FGF-2 (and possibly TGF-β) in response to injury in this model. The interaction of TSP1 with TGF-β is responsible for at least part of the glomerular matrix formation occurring in this model, but does not appear to influence MC proliferation or macrophage accumulation. The link of TSP1 and TGF-β in several experimental kidney disease models as well as the widespread upregulation of TSP1 in experimental inflammatory processes in other organs as well as in human disease, suggests a central role of TSP1 in mediating tissue fibrosis through interaction with latent TGF-β. A therapeutic strategy inhibiting specifically only the TSP1 mediated TGF-β activation in inflammatory disease (similar to the blocking peptides as shown above) may prove to be especially favorable given the known dual effects of TGF-β as a profibrotic as well as an anti-inflammatory cytokine.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

References

1. D'Amico (1987) *QJM* 245, 709–727.
2. Johnson (1994) *Kidney Int.* 45 (6), 1769–82.
3. Galla (1995) *Kidney Int.* 47, 377–387.
4. Border et al. (1994) *N. Engl. J. Med.* 331, 1286–1292.
5. Okuda et al. (1990) *J. Clin. Invest.* 86, 453–462.
6. Border et al. (1990) *Nature* 346, 371–374.
7. Border et al. (1992) *Nature* 360, 361–364.
8. Akaki et al. (1996) *Kidney Int.* 50, 148–155.
9. Isaka et al. (1996) *Nat. Med.* 2, 418–423.
10. Kopp et al. (1996) *Lab. Invest.* 74, 991–1003.
11. Isaka et al. (1993) *J. Clin. Invest.* 92, 2597–2601.
12. Shull et al. (1992) *Nature* 359, 693–699.
13. Sanford et al. (1997) *Development* 124, 2659–2670.
14. Kaartinen et al. (1995) *Nature Genet.* 11, 415–421.
15. Harpel et al. (1992) *Prog. Growth Factor Res.* 4, 321–335.
16. Schultz-Cherry et al. (1993) *J. Cell Biol.* 122, 923–932.
17. Tada et al. (1998) *Nephron* 79, 38–43.
18. Schultz-Cherry et al. (1994) *J. Biol. Chem.* 269, 26775–82.
19. Schultz-Cherry et al. (1995) *J. Biol. Chem.* 270, 7304–7310.
20. Ribeiro et al. (1999) *J. Biol. Chem.* 274, 13586–13593.
21. Crawford et al. (1998) *Cell* 93, 1159–1170.
22. Lawler et al. (1998) *J. Clin. Invest.* 101, 982–992.
23. Bornstein (1995) *J. Cell Biol.* 130, 503–506.
24. Hugo et al. (1995) *Kidney Int.* 48, 1846–1856.
25. Johnson et al. (1991) *Am. J. Pathol.* 138 (2), 313–21.
26. Guo et al. (1997) *J. Peptide Res.* 50, 210–221.
27. Hugo et al. (1997) *J. Clin. Invest.* 100, 786–794.
28. Hugo et al. (1999) (in press *Kidney Int.*).
29. Duijvestijn et al. (1992) *Lab. Invest.* 66 (4), 459–466.
30. Skalli et al. (1986) *J. Cell Biol.* 103 (6), 2787–2796.
31. Kliem et al. (1996) *Kidney Int.* 49, 666–678.
32. Hugo et al. (1996) *J. Clin. Invest* 97 (11), 2499–2416.
33. Pfeffer et al. (1971) *J. Lab. Clin. Med.* 78, 957–962.
34. Schöcklnann et al. (1997) *Kidney Int.* 51, 1228–1236.
35. Johnson et al. (1991) *J. Clin. Invest.* 87 (3), 847–58.
36. Wahl (1992) *J. Clin. Immunol.* 12, 61–74.
37. Iruela-Arispe et al. (1995) *Am. J. Path.* 147, 1715–1727.
38. Sharma et al. (1994) *Am. J. Physiol.* 35, F829–F842.
39. Kitamura et al. (1995) *Kidney Int.* 48,1747–1757.
40. Süto et al. (1996) *Kidney Int.* 50,445–452.
41. Barcellos-Hoff(1996) *J. Mam. Gland Biol. Neoplasia* 1, 351–361.
42. Sime et al. (1997) *J. Clin. Invest.* 100, 768–776.
43. Hugo et al. (1998) *Kidney Int.* 53, 302–311.
44. McGregor et al. (1994) *Am. J. Pathol.* 144, 1281–1287.

TABLE 1

The results of the quantitation for glomerular TGF-β activity, MC matrix expansion (Trichrome stain, collagen I, collagen IV and fibronectin immunostains), MC activation (α-sm actin immunostain), TGF-β and TGF-β-receptors, TSP1, proliferating MC (OX-7/BrdU- and OX-7/PCNA immunostain), microaneurysm formation (PAS stain), macrophage influx (ED-1 immunostain), and proteinuria (mg/24 h). ND means not done and significance values are marked by * ($p < 0.05$).

| anti-Thy 1 model | | 0.3 ml/100 g bw | | |
|---|---|---|---|---|
| | | day 3 | day 5 | day 8 |
| Active TGF-β (colonies > 62 um) | control/SLLK | ND | ND | 380 ± 60 |
| | LSKL | ND | ND | 154 ± 50* |
| | AAWSHW | ND | ND | 220 ± 70* |
| Matrix Trichrome (score 0–3) | control/SLLK | 0.7 ± 0.3 | 1.5 ± 0.2 | 2.3 ± 0.4 |
| | LSKL | 0.4 ± 0.2 | 0.7 ± 0.2 * | 1.2 ± 0.3* |
| | AAWSHW | 0.5 ± 0.3 | 0.9 ± 0.3 * | 1.4 ± 0.4* |
| Matrix Collagen 1 (score 0–4) | control/SLLK | 0.1 ± 0.1 | 2.3 ± 0.5 | 2.0 ± 0.5 |
| | LSKL | 0.1 ± 0.1 | 0.7 ± 0.4* | 0.8 ± 0.5* |
| | AAWSHW | 0.1 ± 0.1 | 0.8 ± 0.6* | 1.0 ± 0.6* |
| Matrix Collagen IV (score 0–4) | control/SLLK | 1.2 ± 0.4 | 3.3 ± 0.4 | 2.6 ± 0.6 |
| | LSKL | 1.0 ± 0.2 | 1.9 ± 0.3* | 1.2 ± 0.4* |
| | AAWSHW | 1.0 ± 0.5 | 2.1 ± 0.6* | 1.3 ± 0.5* |
| Matrix Fibronectin (score 0–4) | control/SLLK | 1.5 ± 0.8 | 3.2 ± 0.4 | 2.3 ± 0.9 |
| | LSKL | 1.2 ± 0.4 | 1.9 ± 0.6* | 0.9 ± 0.6* |
| | AAWSHW | 1.3 ± 0.3 | 1.9 ± 1.2 | 1.2 ± 0.8 |
| MC-activation α-sm actin (score 0–4) | control/SLLK | 0.8 ± 0.4 | 2.9 ± 0.3 | 2.9 ± 0.5 |
| | LSKL | 0.6 ± 0.3 | 2.5 ± 0.4 | 2.4 ± 0.5 |
| | AAWSHW | 1.1 ± 0.5 | 2.8 ± 0.5 | 2.5 ± 0.4 |
| TGF-β1 (score 0–4) | control/SLLK | 0.2 ± 0.2 | 2.6 ± 0.6 | 1.5 ± 0.8 |
| | LSKL | 0.1 ± 0.1 | 1.8 ± 0.6 | 1.7 ± 0.6 |
| | AAWSHW | 0.4 ± 0.2 | 1.9 ± 0.9 | 1.6 ± 1.1 |
| TGF-β2 (score 0–4) | control/SLLK | 0.2 ± 0.1 | 1.6 ± 0.4 | 1.3 ± 0.8 |
| | LSKL | 0.2 ± 0.1 | 1.2 ± 0.6 | 0.6 ± 0.6 |
| | AAWSHW | 0.4 ± 0.3 | 1.1 ± 0.7 | 0.5 ± 0.4 |
| TGF-βRI (score 0–4) | control/SLLK | 0.4 ± 0.2 | 1.9 ± 0.5 | 1.8 ± 0.9 |
| | LSKL | 0.2 ± 0.2 | 1.4 ± 0.3 | 1.4 ± 0.4 |
| | AAWSHW | 0.5 ± 0.3 | 1.9 ± 0.4 | 1.6 ± 0.6 |
| TGF-βRII (score 0–4) | control/SLLK | 0.4 ± 0.3 | 1.9 ± 0.5 | 1.3 ± 0.8 |
| | LSKL | 0.2 ± 0.1 | 1.3 ± 0.3 | 0.9 ± 0.6 |
| | AAWSHW | 0.5 ± 0.5 | 1.4 ± 0.6 | 1.2 ± 0.5 |
| TSP I (score 0–4) | control/SLLK | 0.2 ± 0.2 | 2.0 ± 0.6 | 0.6 ± 0.3 |
| | LSKL | 0.3 ± 0.2 | 1.4 ± 0.6 | 0.5 ± 0.3 |
| | AAWSHW | 0.6 ± 0.2 | 1.5 ± 0.9 | 0.8 ± 0.7 |
| MC-proliferation (OX-7 + /PCNA + cells/ glomerulus) | control/SLLK | 3.6 ± 0.7 | 9.1 ± 1.5 | 4.2 ± 0.5 |
| | LSKL | 3.3 ± 0.6 | 7.9 ± 1.0 | 4.6 ± 0.5 |
| | AAWSHW | 3.1 ± 0.8 | 8.5 ± 1.6 | 3.9 ± 0.8 |
| MC-proliferation (OX-7 + /BrdU + cells/ glomerulus) | control/SLLK | ND | 4.7 ± 0.8 | ND |
| | LSKL | ND | 3.9 ± 0.6 | ND |
| | AAWSHW | ND | 4.6 ± 1.9 | ND |
| Glomerular Micro-aneurysm (in percent) | control/SLLK | 34.0 ± 30.1 | 20.6 ± 22.7 | 6.0 ± 5.9 |
| | LSKL | 16.7 ± 10.0 | 13.8 ± 19.9 | 2.2 ± 2.7 |
| | AAWSHW | 12.2 ± 11.6 | 15.5 ± 11.8 | 1.6 ± 1.8 |
| Macrophages (ED-1 + cells/ glomerulus) | control/SLLK | 4.5 ± 1.6 | 1.9 ± 0.5 | 1.5 ± 0.5 |
| | LSKL | 4.3 ± 2.0 | 1.0 ± 0.6 | 0.7 ± 0.5 |
| | AAWSHW | 3.0 ± 1.8 | 0.9 ± 0.5 | 0.7 ± 0.3 |
| Proteinuria (mg/24 hours) | control/SLLK | ND | ND | 83 ± 40 |
| | LSKL | ND | ND | 24 ± 20* |
| | AAWSHW | ND | ND | 51 ± 50 |

What is claimed is:

1. A method of treating kidney disease in a subject having kidney disease, said method comprising: administering to the subject a pharmaceutically effective amount of a purified peptide, comprising an amino acid sequence Leu-Ser-Lys-Leu (SEQ ID NO. 21), wherein said peptide is derived from thrombospondin, and is operative in inhibiting activation of TGF-β, or a functional derivative thereof, wherein said functional derivative has a free moiety selected from the group consisting of —OH, —SH, —NH$_2$ and —COOH, and a substitution of a hydroxyl by a halogen, and derivatives consisting of ethers, esters, amides not normally part of the peptide.

2. A method according to claim 1, wherein the purified peptide comprises a partial retro-inverso peptide sequence.

3. A method according to claim 1, wherein the purified peptide comprises a full retro-inverso peptide sequence.

4. A method according to claim 1, wherein the purified peptide is conjugated to a water soluble peptide.

5. A method according to claim 1, wherein said administering step further comprises maintaining said pharmaceutically effective amount of a purified peptide within the subject for an amount of time sufficient to reduce glomerular extracellular matrix formation.

6. A method according to claim 1, wherein said administering step further comprises maintaining said pharmaceutically effective amount of a purified peptide within the subject for an amount of time sufficient to suppress proteinuria in the subject.

7. A method of improving renal function in a subject having impaired renal function, said method comprising: administering to the subject a pharmaceutically effective amount of a purified peptide comprising an amino acid sequence Leu-Ser-Lys-Leu (SEQ ID NO. 21), wherein said peptide is derived from thrombospondin, and is operative in inhibiting activation of TGF-β, or a functional derivative thereof, wherein said functional derivative has a free moiety selected from the group consisting of —OH, —SH, —NH$_2$ and —COOH, and a substitution of a hydroxyl by a halogen, and derivatives consisting of ethers, esters, amides not normally part of the peptide.

8. A method according to claim 7, wherein the purified peptide comprises a partial retro-inverso peptide sequence.

9. A method according to claim 7, wherein the purified peptide comprises a full retro-inverso peptide sequence.

10. A method according to claim 7, wherein the purified peptide is conjugated to a water soluble peptide.

11. A method according to claim 7, wherein said administering step further comprises maintaining said pharmaceutically effective amount of a purified peptide within the subject for an amount of time sufficient to reduce glomerular extracellular matrix formation.

12. A method according to claim 7, wherein said administering step further comprises maintaining said pharmaceutically effective amount of a purified peptide within the subject for an amount of time sufficient to suppress proteinuria in the subject.

13. A method of treating a kidney disease having TSP1 mediated TGF-β activation as a component of the disease, said method comprising: administering to the subject a pharmaceutically effective amount of a purified peptide comprising an amino acid sequence Leu-Ser-Lys-Leu (SEQ ID NO. 21), wherein said peptide is derived from thrombospondin, and is operative in inhibiting activation of TGF-β, or a functional derivative thereof, wherein said functional derivative has a free moiety selected from the group consisting of —OH, —SH, —NH$_2$ and —COOH, and a substitution of a hydroxyl by a halogen, and derivatives consisting of ethers, esters, amides not normally part of the peptide.

* * * * *

UNITED STATES PATENT AND TRADEMARK OFFICE
CERTIFICATE OF CORRECTION

PATENT NO. : 6,458,767 B1
DATED : October 1, 2002
INVENTOR(S) : Joanne E. Murphy-Ullrich et al.

It is certified that error appears in the above-identified patent and that said Letters Patent is hereby corrected as shown below:

Title page,
Item [75], Inventors, please delete "Weideu" and insert -- Weiden --;

Column 2,
Line 29, please delete "B" and insert -- B1 --;

Column 4,
Line 28, please delete "CID" and insert -- C/D --;
Line 30, please delete "DIF" and insert -- D/F --;
Line 34, please delete "22)" and insert -- 22)) --;

Column 5,
Line 5, please delete "thereof" and insert -- thereof. --;

Column 9,
Line 56, please delete "Animal Model" and insert -- Animal Model. --;

Column 10,
Line 48, please "Int" and insert -- Int. --;

Column 11,
Line 20, please delete "Mo" and insert -- MO --;

Column 12,
Line 42, please delete "ae novo" and insert -- de novo --;

Column 13,
Line 2, please delete "LSKL" and insert -- (LSKL) --;
Line 3, please delete "(AAWSHW" and insert -- (AAWSHW) --;
Line 4, please delete "(SLLK" and insert -- (SLLK) --;

Column 14,
Line 52, please delete "(2.235.04)" and insert -- (2.2±0.4) --;

Column 15,
Line 3, please delete "±0.3 mi" and insert -- ±0.3 ml --;

UNITED STATES PATENT AND TRADEMARK OFFICE
CERTIFICATE OF CORRECTION

PATENT NO. : 6,458,767 B1
DATED : October 1, 2002
INVENTOR(S) : Joanne E. Murphy-Ullrich et al.

It is certified that error appears in the above-identified patent and that said Letters Patent is hereby corrected as shown below:

Column 16,
Line 45, please delete "süitö" and insert -- sütö --;
Line 59, please delete "canbe" and insert -- can be --;

Column 17,
Line 27, please delete "Bottinger" and -- Bötinger --;

Column 18,
Line 27, please delete "Pathol" and insert -- Pathol. --;

Column 20,
Line 24, please delete "Matrix Collagen 1" and insert -- Matrix Collagen I --;
TABLE 1, please insert the following:
After every instance of "control/SLLK", please insert -- (SEQ. ID NO. 47) --;
After every instance of "LSKL", please insert -- (SEQ. ID NO. 21) --;
After every instance of "AAWSHW", please insert -- (SEQ. ID NO. 22) --.

Signed and Sealed this

Second Day of August, 2005

JON W. DUDAS
*Director of the United States Patent and Trademark Office*

SEQUENCE LISTING

<160> NUMBER OF SEQ ID NOS: 47

<210> SEQ ID NO 1
<211> LENGTH: 6
<212> TYPE: PRT
<213> ORGANISM: Homo sapiens

<400> SEQUENCE: 1

Cys Ser Val Thr Cys Gly
1               5

<210> SEQ ID NO 2
<211> LENGTH: 4
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa is any amino acid

<400> SEQUENCE: 2

Trp Ser Xaa Trp
1

<210> SEQ ID NO 3
<211> LENGTH: 6
<212> TYPE: PRT
<213> ORGANISM: Homo sapiens

<400> SEQUENCE: 3

Gly Gly Trp Ser His Trp
1               5

<210> SEQ ID NO 4
<211> LENGTH: 4
<212> TYPE: PRT
<213> ORGANISM: Homo sapiens

<400> SEQUENCE: 4

Trp Ser His Trp
1

<210> SEQ ID NO 5
<211> LENGTH: 4
<212> TYPE: PRT
<213> ORGANISM: Homo sapiens

<400> SEQUENCE: 5

Lys Arg Phe Lys
1

<210> SEQ ID NO 6
<211> LENGTH: 4
<212> TYPE: PRT
<213> ORGANISM: Artificial Sequence
<220> FEATURE:
<223> OTHER INFORMATION: Synthetic construct

<400> SEQUENCE: 6

His Arg Phe Lys
1

<210> SEQ ID NO 7
<211> LENGTH: 4

```
<212> TYPE: PRT
<213> ORGANISM: Homo sapiens

<400> SEQUENCE: 7

Arg Lys Pro Lys
 1

<210> SEQ ID NO 8
<211> LENGTH: 4
<212> TYPE: PRT
<213> ORGANISM: Artificial Sequence
<220> FEATURE:
<223> OTHER INFORMATION: Synthetic construct

<400> SEQUENCE: 8

Gln Arg Phe Lys
 1

<210> SEQ ID NO 9
<211> LENGTH: 8
<212> TYPE: PRT
<213> ORGANISM: Homo sapiens

<400> SEQUENCE: 9

Lys Arg Phe Lys Gln Asp Gly Gly
 1               5

<210> SEQ ID NO 10
<211> LENGTH: 10
<212> TYPE: PRT
<213> ORGANISM: Homo sapiens

<400> SEQUENCE: 10

Arg Trp Arg Pro Trp Thr Ala Trp Ser Glu
 1               5                  10

<210> SEQ ID NO 11
<211> LENGTH: 17
<212> TYPE: PRT
<213> ORGANISM: Homo sapiens

<400> SEQUENCE: 11

Thr Ala Tyr Arg Trp Arg Leu Ser His Arg Pro Lys Thr Gly Ile Arg
 1               5                  10                  15

Val

<210> SEQ ID NO 12
<211> LENGTH: 17
<212> TYPE: PRT
<213> ORGANISM: Artificial Sequence
<220> FEATURE:
<223> OTHER INFORMATION: Synthetic construct

<400> SEQUENCE: 12

Lys Arg Phe Lys Gln Asp Gly Gly Ala Ser His Ala Ser Pro Ala Ser
 1               5                  10                  15

Ser

<210> SEQ ID NO 13
<211> LENGTH: 14
<212> TYPE: PRT
<213> ORGANISM: Artificial Sequence
<220> FEATURE:
<223> OTHER INFORMATION: Synthetic construct
```

```
<400> SEQUENCE: 13

Lys Arg Phe Lys Gln Asp Gly Gly Ala Ser His Ala Ser Pro
1               5                   10

<210> SEQ ID NO 14
<211> LENGTH: 14
<212> TYPE: PRT
<213> ORGANISM: Homo sapiens

<400> SEQUENCE: 14

Lys Arg Phe Lys Gln Asp Gly Gly Trp Ser His Trp Ser Pro
1               5                   10

<210> SEQ ID NO 15
<211> LENGTH: 17
<212> TYPE: PRT
<213> ORGANISM: Homo sapiens

<400> SEQUENCE: 15

Lys Arg Phe Lys Gln Asp Gly Gly Trp Ser His Trp Ser Pro Trp Ser
1               5                   10                  15

Ser

<210> SEQ ID NO 16
<211> LENGTH: 12
<212> TYPE: PRT
<213> ORGANISM: Homo sapiens

<400> SEQUENCE: 16

Lys Arg Phe Lys Gln Asp Gly Gly Trp Ser His Trp
1               5                   10

<210> SEQ ID NO 17
<211> LENGTH: 12
<212> TYPE: PRT
<213> ORGANISM: Homo sapiens

<400> SEQUENCE: 17

Lys Arg Phe Lys Gln Asp Gly Gly Trp Trp Ser Pro
1               5                   10

<210> SEQ ID NO 18
<211> LENGTH: 3
<212> TYPE: PRT
<213> ORGANISM: Homo sapiens

<400> SEQUENCE: 18

Arg Phe Lys
1

<210> SEQ ID NO 19
<211> LENGTH: 5
<212> TYPE: PRT
<213> ORGANISM: Homo sapiens

<400> SEQUENCE: 19

Trp Asn Asp Trp Ile
1               5

<210> SEQ ID NO 20
<211> LENGTH: 5
<212> TYPE: PRT
<213> ORGANISM: Homo sapiens
```

```
<400> SEQUENCE: 20

Trp Ser Ser Trp Ser
1               5

<210> SEQ ID NO 21
<211> LENGTH: 4
<212> TYPE: PRT
<213> ORGANISM: Homo sapiens

<400> SEQUENCE: 21

Leu Ser Lys Leu
1

<210> SEQ ID NO 22
<211> LENGTH: 6
<212> TYPE: PRT
<213> ORGANISM: Homo sapiens

<400> SEQUENCE: 22

Ala Ala Trp Ser His Trp
1               5

<210> SEQ ID NO 23
<211> LENGTH: 6
<212> TYPE: PRT
<213> ORGANISM: Homo sapiens

<400> SEQUENCE: 23

Asp Gly Trp Ser Pro Trp
1               5

<210> SEQ ID NO 24
<211> LENGTH: 6
<212> TYPE: PRT
<213> ORGANISM: Homo sapiens

<400> SEQUENCE: 24

Gly Gly Trp Gly Pro Trp
1               5

<210> SEQ ID NO 25
<211> LENGTH: 5
<212> TYPE: PRT
<213> ORGANISM: Homo sapiens

<400> SEQUENCE: 25

Trp Ser Pro Trp Ser
1               5

<210> SEQ ID NO 26
<211> LENGTH: 5
<212> TYPE: PRT
<213> ORGANISM: Homo sapiens

<400> SEQUENCE: 26

Gly Trp Ser His Trp
1               5

<210> SEQ ID NO 27
<211> LENGTH: 5
<212> TYPE: PRT
<213> ORGANISM: Homo sapiens
```

```
<400> SEQUENCE: 27

Trp Ser His Trp Ser
1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic construct

<400> SEQUENCE: 28

Trp His Ser Trp Ala Ala
1               5

<210> SEQ ID NO 29
<211> LENGTH: 13
<212> TYPE: PRT
<213> ORGANISM: Homo sapiens

<400> SEQUENCE: 29

Val Thr Cys Gly Gly Gly Val Gln Lys Arg Ser Arg Leu
1               5                   10

<210> SEQ ID NO 30
<211> LENGTH: 4
<212> TYPE: PRT
<213> ORGANISM: Artificial Sequence
<220> FEATURE:
<223> OTHER INFORMATION: Synthetic construct

<400> SEQUENCE: 30

Thr Arg Ile Arg
1

<210> SEQ ID NO 31
<211> LENGTH: 4
<212> TYPE: PRT
<213> ORGANISM: Artificial Sequence
<220> FEATURE:
<223> OTHER INFORMATION: Synthetic construct

<400> SEQUENCE: 31

Ala Arg Phe Lys
1

<210> SEQ ID NO 32
<211> LENGTH: 4
<212> TYPE: PRT
<213> ORGANISM: Artificial Sequence
<220> FEATURE:
<223> OTHER INFORMATION: Synthetic construct

<400> SEQUENCE: 32

Lys Lys Phe Lys
1

<210> SEQ ID NO 33
<211> LENGTH: 4
<212> TYPE: PRT
<213> ORGANISM: Artificial Sequence
<220> FEATURE:
<223> OTHER INFORMATION: Synthetic construct
```

```
<400> SEQUENCE: 33

Lys Gln Phe Lys
1

<210> SEQ ID NO 34
<211> LENGTH: 4
<212> TYPE: PRT
<213> ORGANISM: Artificial Sequence
<220> FEATURE:
<223> OTHER INFORMATION: Synthetic construct

<400> SEQUENCE: 34

Lys Arg Phe Gln
1

<210> SEQ ID NO 35
<211> LENGTH: 4
<212> TYPE: PRT
<213> ORGANISM: Artificial Sequence
<220> FEATURE:
<223> OTHER INFORMATION: Synthetic construct

<400> SEQUENCE: 35

Lys Arg Ala Lys
1

<210> SEQ ID NO 36
<211> LENGTH: 4
<212> TYPE: PRT
<213> ORGANISM: Artificial Sequence
<220> FEATURE:
<223> OTHER INFORMATION: Synthetic construct

<400> SEQUENCE: 36

Lys Arg Tyr Lys
1

<210> SEQ ID NO 37
<211> LENGTH: 4
<212> TYPE: PRT
<213> ORGANISM: Artificial Sequence
<220> FEATURE:
<223> OTHER INFORMATION: Synthetic construct

<400> SEQUENCE: 37

Lys Arg Trp Lys
1

<210> SEQ ID NO 38
<211> LENGTH: 22
<212> TYPE: PRT
<213> ORGANISM: Homo sapiens

<400> SEQUENCE: 38

Ala Ser Leu Arg Gln Met Lys Lys Thr Arg Gly Thr Leu Leu Ala Leu
1               5                   10                  15

Glu Arg Lys Asp His Ser
            20

<210> SEQ ID NO 39
<211> LENGTH: 19
<212> TYPE: PRT
<213> ORGANISM: Homo sapiens
```

```
<400> SEQUENCE: 39

Glu Leu Thr Gly Ala Ala Arg Lys Gly Ser Gly Arg Arg Leu Val Lys
1               5                   10                  15

Gly Pro Asp

<210> SEQ ID NO 40
<211> LENGTH: 6
<212> TYPE: PRT
<213> ORGANISM: Artificial Sequence
<220> FEATURE:
<223> OTHER INFORMATION: Synthetic construct

<400> SEQUENCE: 40

Ser His Trp Trp Ser Ser
1               5

<210> SEQ ID NO 41
<211> LENGTH: 6
<212> TYPE: PRT
<213> ORGANISM: Artificial Sequence
<220> FEATURE:
<223> OTHER INFORMATION: Synthetic construct

<400> SEQUENCE: 41

Gly Gly Trp Ser His Tyr
1               5

<210> SEQ ID NO 42
<211> LENGTH: 6
<212> TYPE: PRT
<213> ORGANISM: Artificial Sequence
<220> FEATURE:
<223> OTHER INFORMATION: Synthetic construct

<400> SEQUENCE: 42

Gly Gly Trp Ser Lys Trp
1               5

<210> SEQ ID NO 43
<211> LENGTH: 3
<212> TYPE: PRT
<213> ORGANISM: Artificial Sequence
<220> FEATURE:
<223> OTHER INFORMATION: Synthetic construct

<400> SEQUENCE: 43

Arg Phe Arg
1

<210> SEQ ID NO 44
<211> LENGTH: 3
<212> TYPE: PRT
<213> ORGANISM: Artificial Sequence
<220> FEATURE:
<223> OTHER INFORMATION: Synthetic construct

<400> SEQUENCE: 44

Arg Trp Arg
1

<210> SEQ ID NO 45
<211> LENGTH: 18
<212> TYPE: PRT
<213> ORGANISM: Homo sapiens
```

```
-continued

<400> SEQUENCE: 45

Lys Arg Phe Lys Gln Asp Gly Gly Trp Ser His Trp Ser Pro Trp Ser
1               5                   10                  15

Ser Cys

<210> SEQ ID NO 46
<211> LENGTH: 12
<212> TYPE: PRT
<213> ORGANISM: Homo sapiens

<400> SEQUENCE: 46

Gly Gly Trp Ser His Trp Ser Pro Trp Ser Ser Cys
1               5                   10

<210> SEQ ID NO 47
<211> LENGTH: 4
<212> TYPE: PRT
<213> ORGANISM: Artificial Sequence
<220> FEATURE:
<223> OTHER INFORMATION: Synthetic construct

<400> SEQUENCE: 47

Ser Leu Leu Lys
1
```